(12) United States Patent
Cloutier et al.

(10) Patent No.: US 9,389,204 B2
(45) Date of Patent: Jul. 12, 2016

(54) METHOD AND SYSTEM OF ULTRASOUND SCATTERER CHARACTERIZATION

(75) Inventors: Guy Cloutier, Québec (CA); François Yu, Montreal (CA); Emilie Franceschini, Marseilles (FR); David Savery, Aix-en-Provence (FR)

(73) Assignee: VAL-CHUM, LIMITED PARTNERSHIP, Montreal, Quebec (CA)

(*) Notice: Subject to any disclaimer, the term of this patent is extended or adjusted under 35 U.S.C. 154(b) by 996 days.

(21) Appl. No.: 12/595,649

(22) PCT Filed: Apr. 10, 2008

(86) PCT No.: PCT/CA2008/000673
§ 371 (c)(1),
(2), (4) Date: Mar. 17, 2010

(87) PCT Pub. No.: WO2008/124923
PCT Pub. Date: Oct. 23, 2008

(65) Prior Publication Data
US 2011/0092817 A1    Apr. 21, 2011

Related U.S. Application Data

(60) Provisional application No. 60/911,738, filed on Apr. 13, 2007, provisional application No. 60/991,431, filed on Nov. 30, 2007, provisional application No. 61/014,991, filed on Dec. 19, 2007.

(51) Int. Cl.
*A61B 8/00* (2006.01)
*G01N 29/06* (2006.01)
(Continued)

(52) U.S. Cl.
CPC .............. *G01N 29/069* (2013.01); *A61B 8/06* (2013.01); *A61B 8/13* (2013.01); *G01N 29/4472* (2013.01);
(Continued)

(58) Field of Classification Search
USPC ......... 600/441–442, 437, 407, 543–457, 465, 600/468–469; 382/181, 191, 187, 225, 282
See application file for complete search history.

(56) References Cited

U.S. PATENT DOCUMENTS 4,265,126 A * 5/1981 Papadofrangakis et al. .................... 73/861.25
4,817,016 A * 3/1989 Thompson et al. ............. 702/39
(Continued)

OTHER PUBLICATIONS

Savery et al (Effect of red cell clustering and anisotropy on ultrasound blood backscatter: A Monte Carlo Study, IEEE Transactions on Ultrasonics, Ferroelectrics, and Frequency Control, vol. 52, No. 1, Jan. 2005.*
(Continued)

*Primary Examiner* — Joel F Brutus
(74) *Attorney, Agent, or Firm* — Norton Rose Fulbright Canada LLP

(57) ABSTRACT

A method for characterizing ultrasound scatterers in a medium comprising providing ultrasound data representing a region of interest comprising a plurality of scatterers in a medium, the plurality of scatterers including clusters of scatterer sub-units, the scatterers having a physical property value to be estimated and the scatterer sub-units having at least one known physical parameter value; modelling the ultrasound data using an at least second order function of a spatial organization parameter defining the spatial organization of the scatterers; and estimating the physical property value of the scatterers from the modelled ultrasound data and the at least one known physical parameter of the sub-units by a regression of the spatial organization parameter as a function of frequency. A system for characterizing ultrasound scatterers is also included.

19 Claims, 16 Drawing Sheets

(51) Int. Cl.
  *A61B 8/06* (2006.01)
  *A61B 8/13* (2006.01)
  *G01N 29/44* (2006.01)
  *G01S 7/52* (2006.01)

(52) U.S. Cl.
  CPC ....... *G01S 7/52036* (2013.01); *G01N 2291/014* (2013.01); *G01N 2291/02408* (2013.01); *G01N 2291/02836* (2013.01)

(56) References Cited

U.S. PATENT DOCUMENTS

| | | | | |
|---|---|---|---|---|
| 5,243,987 | A * | 9/1993 | Shiba | 600/463 |
| 5,348,015 | A * | 9/1994 | Moehring et al. | 600/453 |
| 5,588,032 | A * | 12/1996 | Johnson et al. | 378/8 |
| 6,200,266 | B1 * | 3/2001 | Shokrollahi et al. | 600/438 |
| 2002/0102023 | A1 * | 8/2002 | Yamauchi | 382/199 |
| 2002/0157472 | A1 * | 10/2002 | Stephens et al. | 73/626 |
| 2004/0054283 | A1 * | 3/2004 | Corey et al. | 600/438 |
| 2004/0161141 | A1 * | 8/2004 | Dewaele | 382/132 |
| 2005/0101846 | A1 * | 5/2005 | Fine et al. | 600/316 |

OTHER PUBLICATIONS

International Search Report, PCT/CA2008/000673, Jul. 17, 2008.
Beng-Ghee Teh et al., "Modeling and Analysis of Ultrasound Backscattering by Spherical Aggregates and Rouleaux of Red Blood Cells", IEEE Transactions on Ultrasonics, Ferroelectrics, and Frequency Control, vol. 17, No. 4, pp. 1025-1035, Jul. 2000.
Romijn Leo R. et al., "Estimation of Scatterer Size From Backscattered Ultrasound: A Simulation Study" IEEE Transactions on Ultrasonics, Ferroelectrics, and Frequency Control, vol. 36, No. 6, pp. 593-606, Nov. 1989.

* cited by examiner

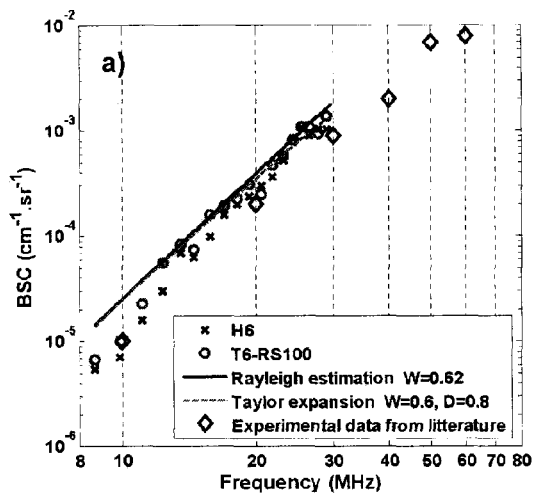 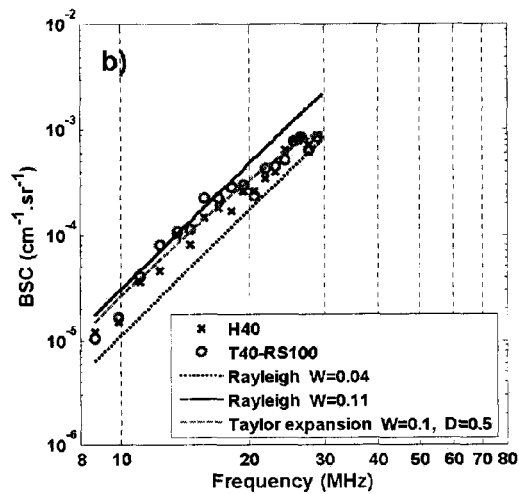
Figure 3(a)	Figure 3 (b)
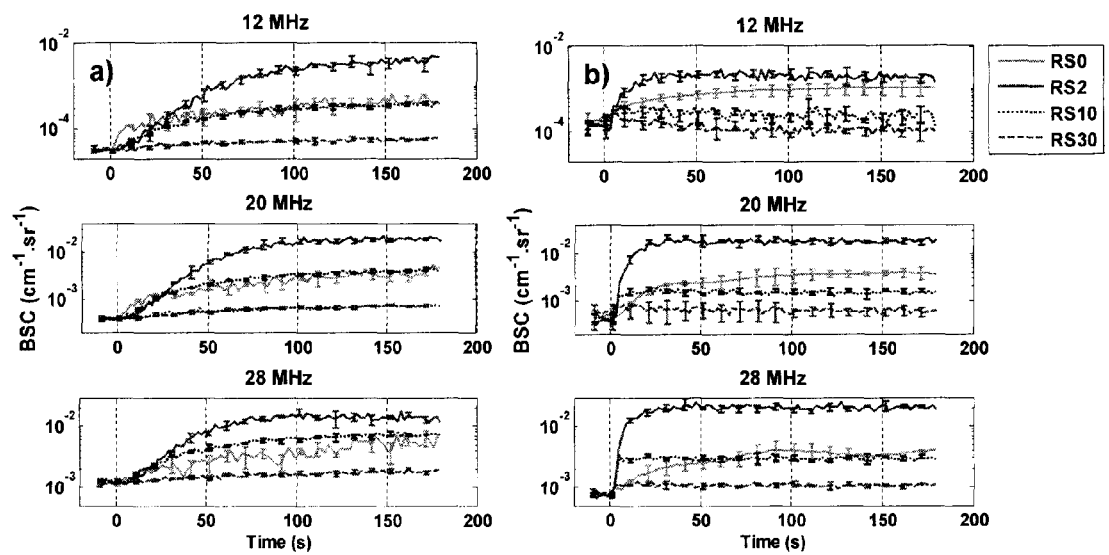
Figure 4(a)	Figure 4 (b)

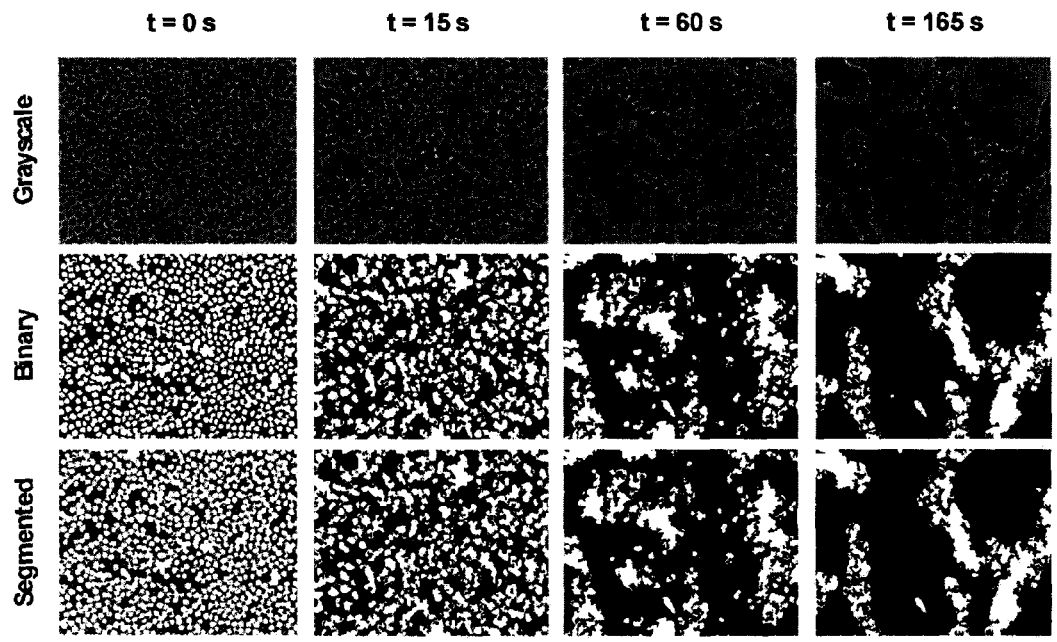
Figure 7 (a)   Figure 7 (b)   Figure 7 (c)   Figure 7 (d)
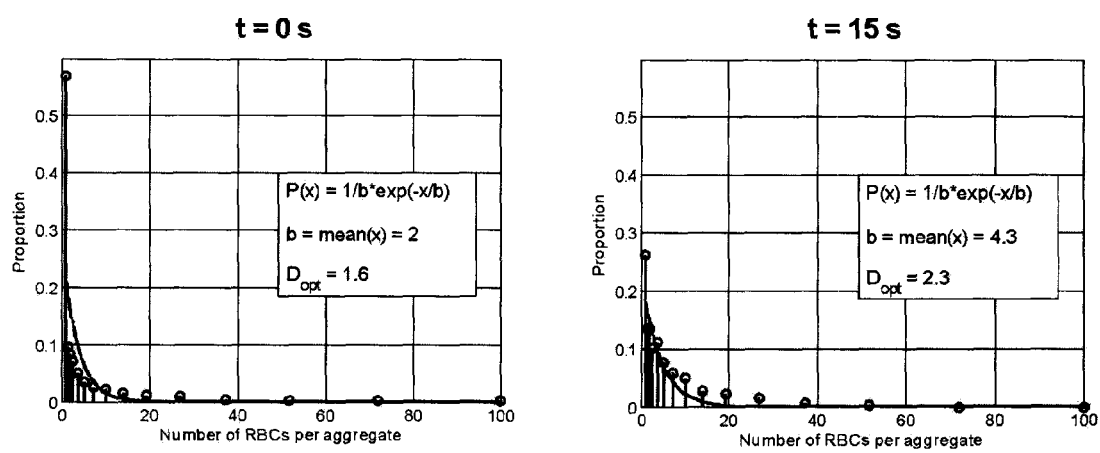
Figure 8(a)                           Figure 8(b)

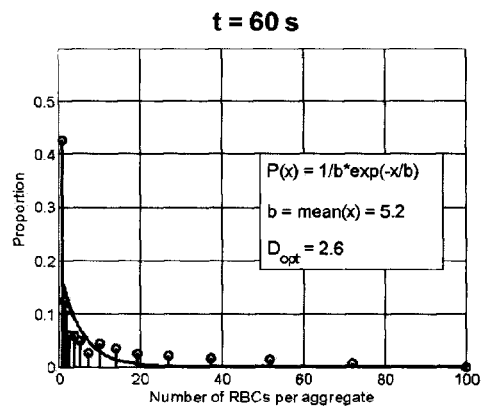
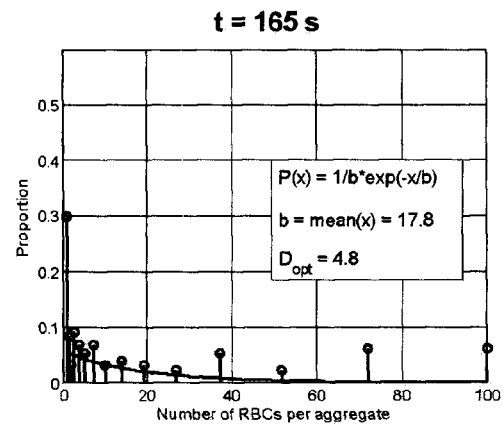
Figure 8(c)    Figure 8(d)
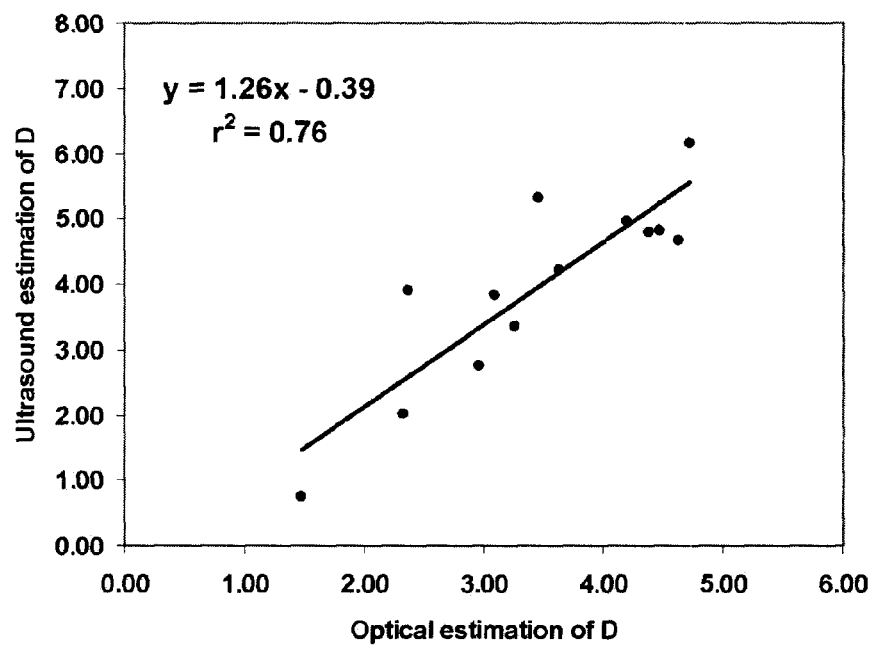
Figure 9

B-mode

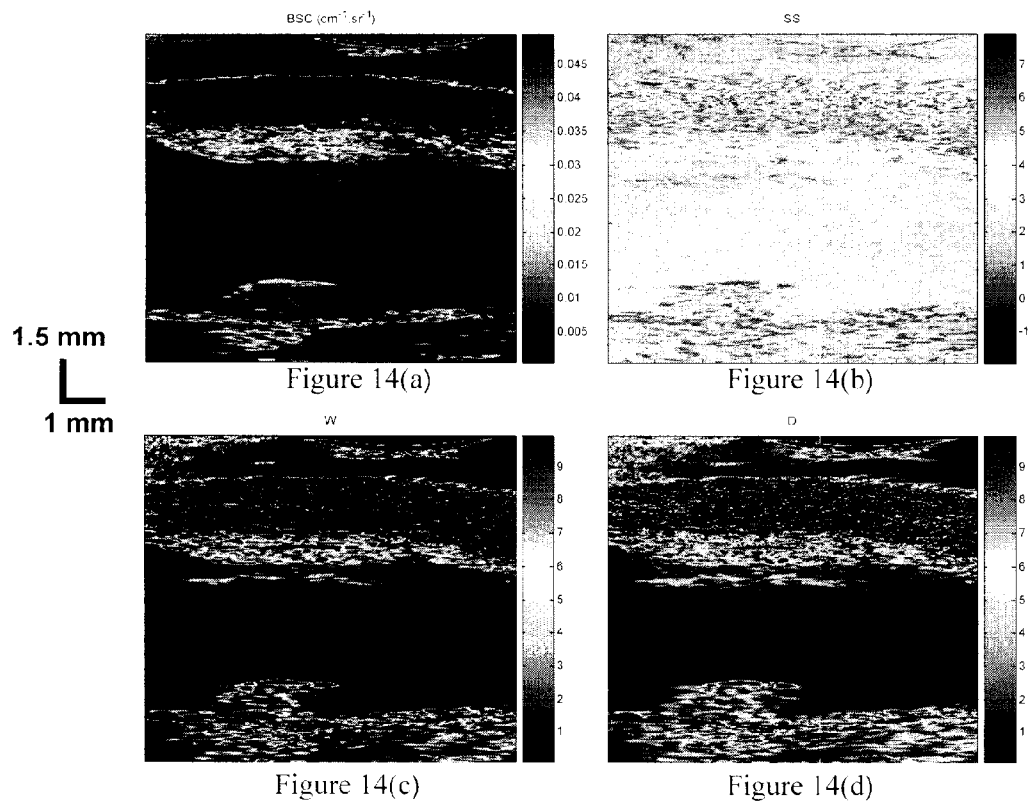
Figure 14(a)  Figure 14(b)
Figure 14(c)  Figure 14(d)
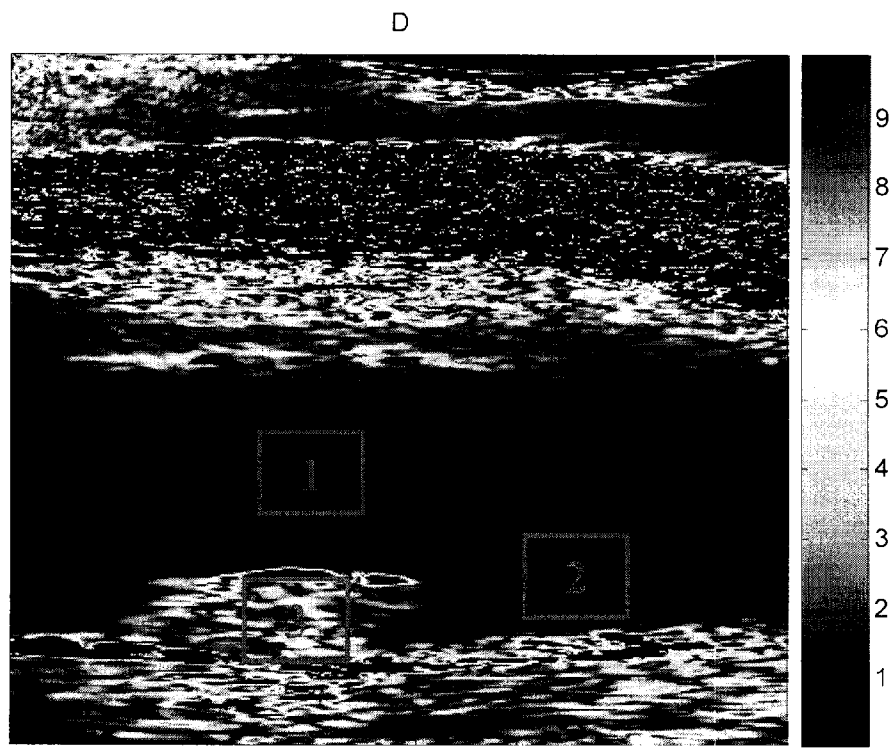
Figure 15

|   | BSC | SS | W | D |
|---|---|---|---|---|
| 1 | 0.00040097 | 3.5399 | 0.09344 | 0.44411 |
| 2 | 0.00049298 | 3.3548 | 0.13389 | 0.58136 |
| 3 | 0.0085497 | 2.648 | 4.5361 | 3.8489 |
Figure 16
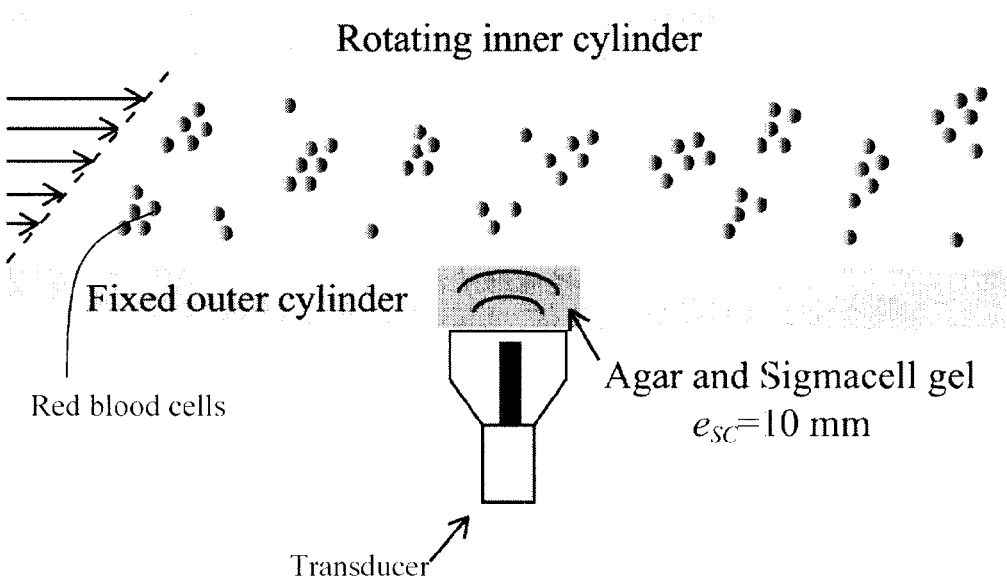
Figure 17
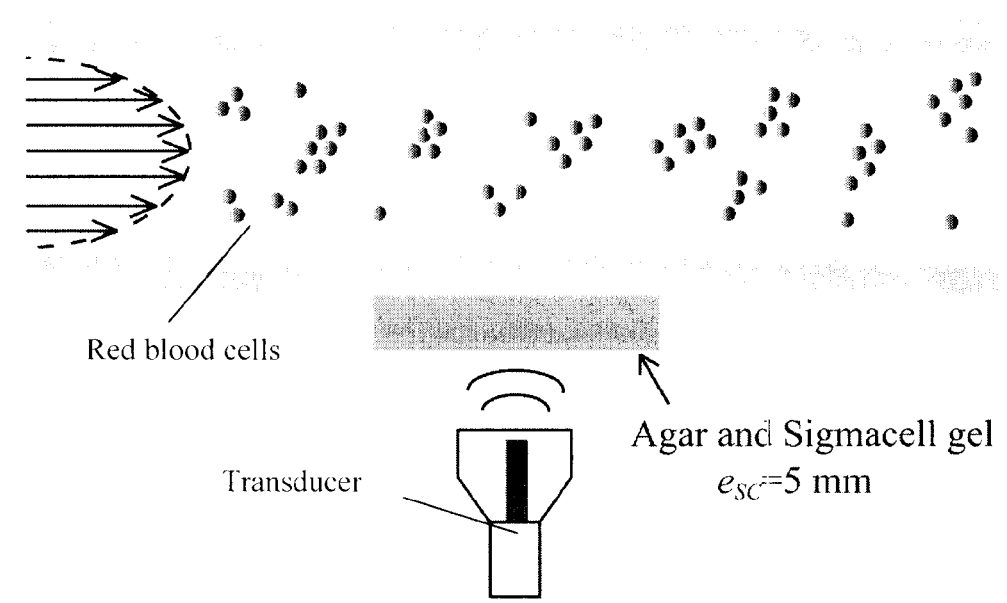
Figure 18

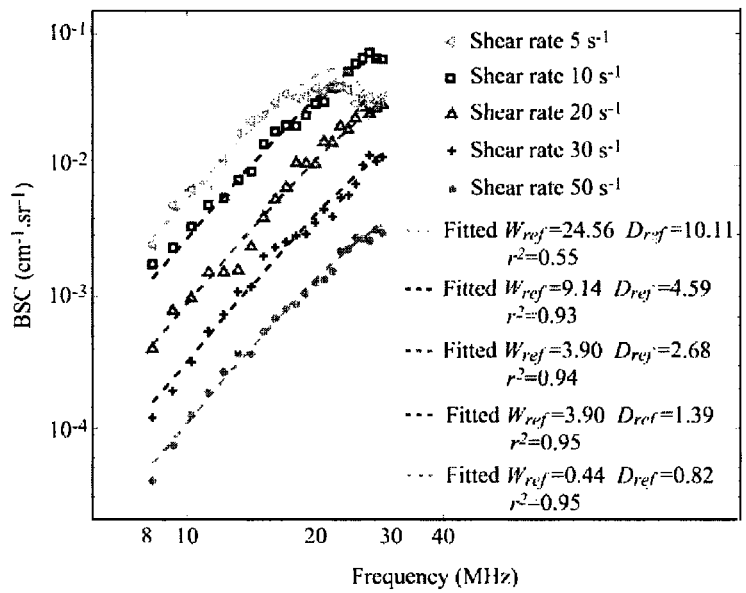
Figure 21
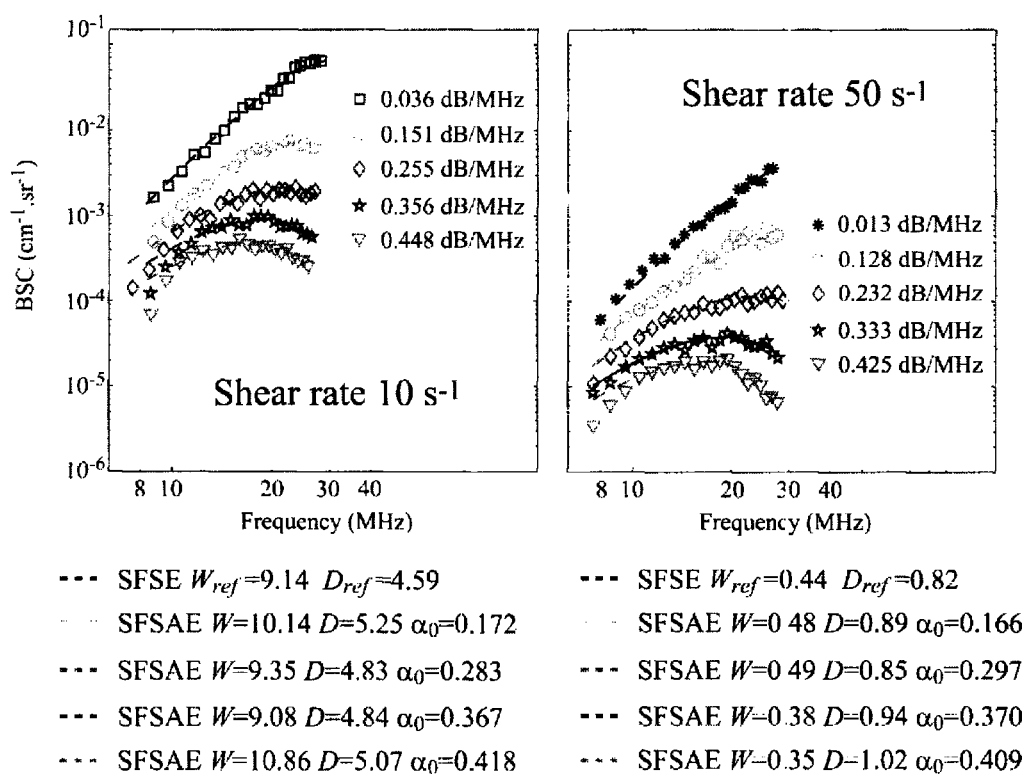
Figure 22(a)
Figure 22(b)

- ⊟ SFSE with compensation for blood attenuation (0% SC)
- SFSAE (1% SC i.e. 0.206 dB/MHz)    ★ SFSAE (2% SC i.e. 0.412 dB/MHz)
- ◇ SFSAE (1.5% SC i.e. 0.310 dB/MHz)    ▽ SFSAE (2.5% SC i.e. 0.501 dB/MHz)

METHOD AND SYSTEM OF ULTRASOUND SCATTERER CHARACTERIZATION

CROSS-REFERENCE TO RELATED APPLICATION(S)

The present application is a National Stage Entry of PCT/CA2008/000673 filed on Apr. 10, 2008 which claims priority on U.S. Provisional Patent Application No. 61/014,991, filed on Dec. 19, 2007, U.S. Provisional Patent Application No. 60/991,431, filed on Nov. 30, 2007, and U.S. Provisional Patent Application No. 60/911,738, filed on Apr. 13, 2007, all incorporated herein by reference.

FIELD OF THE INVENTION

The present invention generally relates to a method and a system of ultrasound scatterer characterization.

BACKGROUND OF THE INVENTION

Ultrasound techniques are commonly used as non-invasive or non-destructive diagnostic tools in a range of industries including medicine, foodstuffs, pharmaceuticals, petrochemicals, chemicals and materials processing. In known ultrasound methods, ultrasound echoes are transmitted to scatterers in a medium and backscattered or scattered echoes are detected. Ultrasound parameters such as backscattering coefficient, angular scattering, attenuation, speed of sound, material nonlinearity and statistics can then be used to reveal intrinsic material properties of the scatterers or the medium such as microstructure and/or composition. In the case of ultrasound imaging of a biological tissue, the radio-frequency ultrasound signal backscattered by the components of the tissue has been used to extract quantitative properties of the scatterers to reveal tissue properties such as the correlation length of the medium. This method and the other aforementioned approaches have been used successfully to detect and diagnose medical conditions, such as prostate cancer, early Duchenne muscular dystrophy, cell apoptosis and carcinomas.

However, these methods are not suitable for all applications. They are particularly unsuitable for characterizing dense concentrations of scatterers in a medium such as dense suspensions of particles. It is desirable to obtain quantitative information regarding the physical dimensions of such scatterers. For example, in two-phase systems such as solid particles/droplets of insoluble liquid/gas bubbles in a fluid, it is desirable to quantitatively characterize the suspensions in terms of the suspended particle size, concentration and other physical parameters. One such application is in medical diagnostics where the aggregation of red blood cells is known to be an independent risk factor of circulatory related disorders such as thrombosis, atherosclerosis and valvular heart disease. Also, the presence and size of embolisms in the blood vessels of a patient can be indicative of their risk of suffering a stroke. In industrial and food processing applications, particle size and shape characterizations are important in the quality control of many manufacturing processes such as slip casting, catalytic processes, fermentation processes, paper and paint manufacturing, as well as in the monitoring of emulsions and colloids and wear and failure of equipment parts.

In many applications such as medical ultrasound imaging, food processing and non destructive testing, the medium to monitor is composed of many weak scatterers. In pulse-echo mode, these scatterers are weak in the sense that the echoes they generate have a small amplitude in comparison to the transmitted sound wave, i.e. their acoustic parameters are closed from the acoustic parameters of their surrounding medium. For weak scatterers in a relatively dilute medium, the power of the backscattered signal increases with increasing scatterer concentration and size. This linear relationship has been exploited to monitor relative increases or decreases in the scatterer size and concentration. However, these known ultrasound techniques cannot provide quantitative or absolute physical parameters or accurate qualitative estimates of the physical parameters of the scatterers in dense medium.

The quantitative characterization of scatterers by ultrasound is further compounded by signal loss due to attenuation by intervening material between the scatterers being characterized and an ultrasound probe. Attenuation can be particularly problematic in the characterization of biological material because of the frequency-dependent attenuation due to intervening tissue layers that distorts the frequency dependence of scattering from the tissue microstructure.

In known attenuation compensation methods, the backscatter coefficient is compensated a posteriori with known values of attenuation based on the estimated thicknesses of the intervening attenuating layers. However, this method can result in inaccurate compensation, especially in the case of characterization of biological material as intervening tissue layer attenuations can vary between layers and can also vary between patients. It is also known to first evaluate the attenuation of the intervening tissue layers and then compensate a posteriori the backscatter coefficient with this attenuation value. However, the attenuations of each intervening layer between the ultrasound probe and the site of the scatterers being characterized must be estimated by a separate measurement technique which means that the compensation cannot be in real-time or performed by a single device. Furthermore, these methods assume strong hypotheses on spatial tissue homogeneity which can lead to inaccuracies.

A further limitation of known prior art ultrasound scatterer characterization techniques is that some of them rely on sampling a bulk suspension to be tested (i.e. "in vitro" methods). However, these in vitro methods cannot provide real-time analysis as samples from a bulk suspension must be isolated to be analyzed. This is undesirable in the case of manufacturing processes where the process must be interrupted to take a sample, or where the substance concerned is toxic, caustic, hot or pressurized. Sampling can also introduce contamination into the bulk or can dilute the bulk. Also, it can introduce sampling errors if the sample taken is not indicative of the bulk. In the case of medical applications, such as detecting red blood cells or other particulates in blood samples, there is the obvious drawback of having to take a blood sample from the patient and the associated health and safety issues for both the patient and the person taking the blood. In addition, it is believed that the microstructure of blood, particularly the aggregation of red blood cells, varies within the vasculature according to flow conditions and local release of substances promoting aggregation. It is therefore preferable to measure in situ and in vivo, the state of aggregation of the red blood cells, as well as other scatterers.

Therefore, there is a need for an improved method and system for ultrasound scatterer characterization.

SUMMARY OF THE INVENTION

An object of the present invention is to provide an improved method and system for ultrasound scatterer characterization. The present invention reduces the difficulties and disadvantages of the aforesaid prior art by providing a novel approach to characterizing scatterers based on ultrasound scattering or backscattering measurements which may be automated and operated in real-time.

According to a broad aspect of the invention, there is provided a method for characterizing ultrasound scatterers in a medium. The method comprises providing ultrasound data representing a region of interest comprising a plurality of scatterers in a medium, the plurality of scatterers including clusters of scatterer sub-units, the scatterers having a physical property value to be estimated and the scatterer sub-units having at least one known physical parameter value; modelling the ultrasound data using an at least second order function of a spatial organization parameter defining the spatial organization of the scatterers; and estimating the physical property value of the scatterers from the modelled ultrasound data and the at least one known physical parameter of the sub-units by a regression of the spatial organization parameter as a function of frequency. The ultrasound data may represent an ultrasound power spectrum of the region of interest. In other words, the model of the frequency ultrasound data is valid at least at the second order of the frequency.

The method may include at least one or all of the additional steps of transmitting ultrasound echoes to the region of interest, detecting the scattered or backscattered echoes as the ultrasound data or converting the detected signals to the ultrasound data, displaying the estimated physical property value of the scatterers, and providing an alert responsive to whether the estimated physical property value of the scatterers matches, approaches, falls below or falls above a predefined value. The ultrasound data may be derived from ultrasound backscattering measurements or scattering measurements of the scatterers in the medium. Quantitative or qualitative physical parameter values can be obtained.

Advantageously, the ultrasound data can be based on the Born approximation and the spatial organization parameter can be a structure factor. A structure factor is related to the probability of finding two scatterers separated by a certain distance. The regression can be a least squared approximation of, for example, a polynomial fitting such as a Taylor approximation. The Taylor approximation can be a second order Taylor approximation of the form: $S(k,\theta) \approx C_0 + kC_1(\theta) + k^2C_2(\theta)$, where S is the spatial organization parameter, k is the wave vector, $\theta$ is an angle, and $C_o$, $C_1$ and $C_2$ are constants. The Applicant has found that a second order Taylor approximation yields surprisingly and unexpectedly good results compared with higher orders, although higher orders may still yield useful physical parameter values.

The scatterer physical property to be estimated may be non-homogeneous i.e. scatterer clusters of different sized and/or mixture of scatterer clusters and single scatterer sub-units. In this case, the estimated physical property value is an average or mean value of the scatterer property. Advantageously, estimating the physical property value of the scatterer clusters can occur in real-time to obtain absolute values of the physical property. Scatterer clusters can comprise two or more whole or partial scatterer sub-units joined or merged or otherwise associated with one another.

In one application of the method, the scatterer sub-units and/or the scatterer clusters are weak scatterers in a dense concentration in the medium. The scatterers and the scatter sub-units may be particles suspended in a medium. The application is particularly, although not exclusively, applicable to dense suspensions of weak scattering sub-units and/or clusters of weak scattering sub-units, for example, red blood cells and/or clusters of red blood cells in blood. The method is also applicable to a low density of scatterers for estimating descriptive parameters of the scatterer sub-units and/or clusters of weak scattering sub-units.

In one embodiment, the ultrasound data represents an ultrasound backscatter coefficient (BSC), and the physical property value to be estimated is the packing factor W and the diameter D of the scatterers, the method comprising applying:

$$BSC(-2k) = \frac{1}{3\pi}HC^2k^4a^3\left[3\frac{\sin(2ka) - 2ka\cos(2ka)}{(2ka)^3}\right]^2 \times [W - 2.4D^2a^2k^2]$$

where k is a wave vector. In this embodiment, scatter sub-unit radius a and an impedance mismatch C between the scatterer sub-units and the medium is known. For this ultrasound backscatter embodiment, the method may further comprise transmitting ultrasound energy to the region of interest to obtain backscattered ultrasound radio-frequency signals, digitizing said ultrasound radio-frequency signals, Fourier transforming the digitized ultrasound radio-frequency signals and squaring the amplitude to obtain the backscatter coefficient.

In another embodiment, modelling the ultrasound data includes consideration of an attenuation of the scatterers and the medium, the method further comprising estimating the attenuation at the same time as estimating the physical property value of the scatterers. Simultaneously estimating the attenuation and the physical property value can comprise minimizing a cost function which is a mean quadratic difference between the ultrasound data provided and the modelled data. In this embodiment, the ultrasound data as a function of the spatial organization parameter is based on the Born approximation and the spatial organization parameter is a structure factor. The ultrasound data may represent an ultrasound backscatter coefficient (BSC). In this case, the physical parameter value to be estimated can be the packing factor W and the diameter D of the scatterers, the method comprising applying:

$$BSC(-2k) = \frac{1}{3\pi}HC^2k^4a^3\left[3\frac{\sin(2ka) - 2ka\cos(2ka)}{(2ka)^3}\right]^2 \times [W - 2.4D^2a^2k^2] \times [e^{-4\alpha_0 f^i}]$$

where k is a wave vector, $[e^{-4\alpha_0 f^i}]$ the frequency-dependent attenuation, $\alpha_0$ is the attenuation coefficient, and f is the frequency. For this ultrasound backscatter embodiment, the method may further comprise transmitting ultrasound energy into the region of interest to obtain backscattered ultrasound radio-frequency signals, digitizing said ultrasound radio-frequency signals, Fourier transforming the digitized ultrasound radio-frequency signals and squaring the amplitude to obtain the ultrasound backscatter coefficient.

From another aspect, there is provided a method for characterizing ultrasound scatterers in a medium, the method comprising providing ultrasound data representing a region of interest comprising a plurality of scatterers in a medium, the plurality of scatterers including clusters of scatterer sub-units, the scatterers having a physical property value to be estimated and the scatterer sub-units having at least one known physical parameter value; modelling the ultrasound data using an at least second order function of a spatial organization parameter defining the spatial organization of the scatterers; and simultaneously estimating an attenuation of the scatterers and the medium and the physical property value of the scatterers from the modelled ultrasound data and the at least one known physical parameter of the scatterer sub-units by a mean quadratic difference between the ultrasound data provided and the modelled data. The ultrasound data may represent an ultrasound power spectrum of the region of interest.

From yet another aspect, there is provided a method for characterizing ultrasound scatterers in a medium, the method comprising: providing ultrasound data representing a region of interest comprising a plurality of scatterers in a medium, the plurality of scatterers including clusters of scatterer sub-units, the scatterers having a physical property value to be estimated and the scatterer sub-units having at least one known physical parameter value; modelling the ultrasound data using a second order model of a structure factor defining the spatial organization of the scatterers; and estimating the physical property value of the scatterers from the modelled ultrasound data and the at least one known physical parameter of the scatterer sub-units by a least mean squared polynomial fitting of the structure factor as a function of frequency.

From a yet further aspect, there is provided use of any of the above methods for monitoring clustering of scatterer sub-units or unclustering of scatterer clusters. Advantageously, the monitoring can be in real-time and can be used as in vivo and in vitro diagnostic tools.

From another aspect, there is provided a computer readable memory having recorded thereon statements and instructions for execution by a computer to carry out any of the above methods for characterizing ultrasound scatterers.

There is also provided a system for characterizing ultrasound scatterers in a medium, the system comprising: a transmitting means for transmitting an ultrasound signal to a region of interest, the region of interest comprising a plurality of scatterers in a medium, the plurality of scatterers including clusters of scatterer sub-units, the scatterers having a physical property value to be estimated and the scatterer sub-units having at least one known physical parameter value; at least one detecting means for detecting a scattered or a backscattered ultrasound signal; and a processing means for converting the detected ultrasound signal to ultrasound data representing the region of interest, modelling the ultrasound data using an at least second order function of a spatial organization parameter defining the spatial organization of the scatterers, and estimating the physical property value of the scatterers from the modelled ultrasound data and the at least one known physical parameter of the scatterer sub-units by a regression of the spatial organization parameter as a function of frequency. The ultrasound data may represent an ultrasound power spectrum of the region of interest. The transmitting means may be a transmitter, the detecting means may be a detector and the processing means may be a processor.

Embodiments of the novel method and system of the present invention are particularly suited, but not limited, to characterizing weak scatterers in a homogenous medium, such as a suspension of cells and their agglomerates in blood. As used herein, a suspension refers to solid scatterers suspended in a fluid, typically a liquid. By solid scatterer, it is meant any particle or object containing solid material and includes mixed phase particles such as hollow particles which may or may not contain a fluid. The liquid of the suspension can be any kind of liquid depending on the application, such as body fluids, water, polymers or industrial slurries. The scatterers in a suspension can generally be any size or shape and can include entrained air or liquid material. In many applications, the suspension will be complex, having scatterers of non-uniform size and shape. Scatterer suspensions where the linear increase of the power with the concentration does not apply, e.g. particles at a high concentration in dense media, can also be characterized using the present method.

The present method also applies to weak scatterers in a solid medium, such as biological tissue.

Advantageously, the method is not limited to the quantification of ultrasound data e.g. backscatter coefficient (BSC) and its frequency dependence (spectral slope, y-intercept, mid-band fit), unlike known prior art methods which can only provide ultrasound related parameters that are difficult to interpret and are also intrinsically dependent on the frequency that is used. The present approach, on the other hand, allows these ultrasound related parameters to be transformed into physically representative quantitative data, e.g. absolute values of a packing factor W and an average cluster (aggregate) non-dimensional size D. Embodiments of the present invention therefore allow comparisons of studies in different frequency ranges and comparison with results from other fields of study.

The case where attenuating medium or media are introduced between an ultrasound probe and the region of interest is also considered by an embodiment of the present invention. Thus, an estimate of a physical parameter value of scatterers can be obtained with or without attenuating media such as layers between the ultrasound probe and scatterers (e.g. particles, homogeneous or heterogeneous tissue) to be characterized. Advantageously, the attenuating properties of the intervening matter between the particles being measured and the ultrasound probe can be estimated (i.e. compensated for) at the same time as characterizing the particles. This is particularly advantageous in the case of the intervening matter being variable in attenuating properties and its effects being difficult to predict such as when the intervening matter is soft tissue such as human or animal tissue or plant matter. Advantageously, the attenuation effect is estimated and compensated for without having to separately measure the attenuation of the intervening material. The model can be successfully applied to many types of samples regardless of the intervening material. However, it is particularly suited to the in vivo detection of blood cells through the skin of a patient and their aggregation. Advantageously, the packing factor parameter, W, the fractal dimension (e.g. a fractal diameter) of particles or particle aggregates, D, and the attenuation can be estimated simultaneously from ultrasound data derived from detected echoes. This is in contrast to known methods of compensating for attenuation where a compensation for attenuation is applied on ultrasound signals after ultrasound measurement. In these known methods, the attenuation value is based on published data of which the most appropriate attenuation is chosen for that given situation. Another known method is to measure attenuation at a second phase with other instrumentation.

One advantage of embodiments of the present invention is that they can be applied in situ and in vivo non-destructively so that the scatterers to be characterized need not be sampled. Also, scatterers can be characterized in real-time to provide a "live" monitoring capability. Furthermore, accurate and absolute physical parameter values can be obtained to represent the real-life situation of the scatterers.

For example, an embodiment of the present invention can be used to monitor red blood cell aggregation which can be a marker of inflammation. Inflammation may be encountered in patients with obesity, diabetes, atherosclerosis, rheumatoid arthritis, rheumatic fever, bacterial infection, meningitis, neonatal illness and pneumonia, inter-current sepsis, septic shock, cancer, heart disease, those at risk of developing deep vein thrombosis and pulmonary embolisms (e.g., hospitalized immobile patients), and those undergoing cancer treatment and surgery, such as heart surgery, and patients with HIV. The inflammatory response accompanied by abnormal levels of red blood cell aggregation can lead to an acute vaso-occlusive crisis or thrombotic complications which may be fatal. Platelet aggregation occurring in response to a blood vessel injury can also be monitored with ultrasound and characterized by an embodiment of the present invention. Monitoring and measuring red blood cell aggregation may also be valuable in assessing the response to therapy and changes in the pathological state of many chronic inflammatory diseases that are difficult to monitor clinically. This is particularly true of rheumatoid arthritis, polymyalgia, giant cell arthritis, inflammatory bowel disease, systemic vasculitis, chronic migraine, antibacterial therapy, genetic blood diseases as beta-thalassemia and sickle cell anaemia, malaria, and future coronary events in patients with unstable angina or after coronary occlusion or post-surgery. Aggregation of red blood cells and their disaggregation (unclustering) can therefore be detected and monitored in vivo as red blood cell clusters are moving in a blood vessel. In this way, bedside monitoring of red blood cell aggregation in patients in an emergency or in intensive care units to allow immediate diagnosis and treatment is possible. Self-monitoring is also possible.

Numerous other applications are also envisaged where it is desired to obtain realistic and useful estimates of the physical parameters of scatterers (e.g. size of scatterers, volume concentration and density of scatterers, compressibility and packing organization of scatterers, etc.). Examples include platelet clustering in blood, paint and other chemical particle clustering and de-clustering, milk and other food particle clustering and de-clustering, as well as scatterer suspensions in other applications such as foodstuff processing, pharmaceuticals, material processing, waste treatment, and other industrial processes. Therefore, although the present invention is particularly well suited to characterizing agglomerated red cell particles in a blood suspension, it is not limited to such.

Before describing embodiments of the system and method of the invention in more detail, it is appropriate to discuss the development underlying these embodiments which originated from the Applicant desires obtaining quantitative information about the aggregation or clustering of blood elements such as red blood cells and platelets in blood, although the present invention clearly has a much broader application.

It is known that red blood cell aggregates form complex three-dimensional rouleaux structures, and that the quantitative in vivo characterization of red blood cell aggregation may be used as a diagnostic tool. One difficulty in ultrasonic blood characterization resides in the fact that blood is a dense medium (approximately 5 million erythrocytes/mm³) which introduces a non-linear relationship between the backscattered ultrasound power and the scatterer concentration. The red blood cell volume concentration (hematocrit) normally ranges from 35% to 45%, and non-linear acoustic effects become important above approximately 10% hematocrit. Another challenge of ultrasonic blood characterization is to consider clustering particles in the blood as red blood cell aggregates, and mixed red blood cell and platelet aggregates.

The non-linear hematocrit dependence of the backscattering coefficient (BSC) has been studied for non-aggregating red blood cell suspensions. It is well described for Rayleigh scatterers at frequencies up to 90 MHz by the Perkus Yevick packing factor $W_{PY}$. In the frequency domain, the ultrasound spectrum of non-aggregating red blood cells presents a spectral slope of four. The spectral slope is the linear slope of the backscatter coefficient (BSC) as a function of frequency on a log-log scale. When considering aggregating red blood cells, an increase in the effective scatterer size caused by the red blood cell rouleaux formation or an increase of the insonifying ultrasound frequency (to achieve better resolution) both increase the adimensional ka product and restrain the validity of the Rayleigh scattering theory and Perkus Yevick approximation (k is the ultrasound wave number, and a is the mean radius of individual scatterer sub-units).

Suspended red blood cells in a saline solution (no aggregation) can be acoustically considered as a collection of weak scatterers surrounded (e.g. suspended or embedded) in a homogeneous medium. Using the Born approximation and at a low frequency, the backscattered power is given by:

$$BSC(-2k) = m\sigma_b(-2k)W, \quad (1)$$

where m is the number density of scatterers, $\sigma_b$ is the backscattering cross section of a single scatterer sub-unit, W is the packing factor and k is the wave vector which is a function of frequency. For suspended red blood cells in saline, all parameters in Equation 1 can be determined analytically. When the hematocrit is known by micro centrifugation, m is given by $m = H/V_s$, where $V_s$ is the volume of a red blood cell (typically 87 μm³). The backscattering cross-section $\sigma_b$ of a Rayleigh scatterer can be estimated by:

$$\sigma_b(-2k) = \frac{1}{4\pi^2} V_s^2 C^2 k^4 \left(3\frac{\sin(2ka) - 2ka\cos(2ka)}{(2ka)^3}\right)^2, \quad (2)$$

where a is the radius of a sphere of volume $V_s$, and C is the acoustical relative impedance mismatch between the red blood cell and its suspending medium (saline or plasma), which depends on the density and compressibility of the considered media, hence $$C = \frac{Z_{RBC} - Z_{Plasma}}{Z_{Plasma}},$$

where Z refers to the acoustical impedance.

Values of some physical properties of blood, such as density ρ, adiabatic compressibility κ and acoustic impedance Z, have been reported in the literature and so are known. The packing factor W has also previously been studied for non aggregating scatterers. The packing factor W was shown to reflect the increase in spatial correlation among particles with increasing particle number (or hematocrit). It is also influenced by the flow conditions that typically govern flow disturbance or turbulence and aggregation of scatterers. Expressions of the Perkus Yevick packing factor $W_{PY}$ (hard particles) have previously been proposed for packed spheres ($W_{PYs}$) and cylinders ($W_{PYc}$). They are functions of the hematocrit H.

$$W_{PYs}(H) = \frac{(1-H)^4}{(1+2H)^2} \quad (3)$$

$$W_{PYc}(H) = \frac{(1-H)^3}{(1+H)^2} \quad (4)$$

The cylinder prototype (Equation 4) has been reported to provide the best fitting with experimental measurements for suspended (non aggregating) red blood cells up to physiological hematocrits. However, this Rayleigh theoretical approach cannot be used when aggregating red blood cells or other scatterers are considered, especially when the frequency is increased as the assumption that the scatterer size is negligible compared to the acoustical wavelength is no longer valid.

To attempt to address this, the Applicant had previously modelled the backscatter power increase with red blood cell aggregation in the non-Rayleigh regime based on a structure factor, S(−2k), which characterizes the spatial organization of the scatterers in the frequency domain, which they found could explain the frequency dependence of aggregating red blood cells in the non-Rayleigh regime (Fontaine, I. et al "Modeling the frequency dependence (5-120 MHz) of ultrasound backscattering by red cell aggregates in shear flow at a normal hematocrit," Journal of the Acoustical Society of America 113(5), 2893-2900 (2003), the content of which is herein included by reference).

This approach was based upon the generalized form of Equation 1, namely:

$$BSC(-2k) = m\sigma_b(-2k)S(-2k). \quad (5)$$

With this formalism, the number density of scatterers m and the backscattering cross-section of a single red cell or scatterer $\sigma_b$ remain constant, and changes in backscattered power are entirely caused by variations of the structure factor S(−2k), which is by definition the Fourier transform of the pair correlation function g(r) (Twersky, V., "Low-frequency scattering by correlated distributions of randomly oriented particles," Journal of the Acoustical Society of America 81(5), 1609-1618 (1987)):

$$S(-2k) = 1 + m\int(g(r)-1)e^{-j2kr}dr. \quad (6)$$

In this expression, g(r) represents the probability of finding two particles separated by a distance r. Equations 6 shows that a variation in the microscopic organization of particles (due to changes in hematocrit, changes in the state of aggregation or changes in flow conditions) modifies S(−2k) and therefore BSC. From Equation 6, it can be shown that the low frequency limit of S(−2k) is the packing factor W:

$$S(-2k)|_{k\to 0} = 1 + m\int(g(r)-1)dr = W. \quad (7)$$

Under Rayleigh conditions (low ka regime), Equation 5 therefore directly reduces to Equation 1 provided the low frequency structure factor limit reduces to W, i.e. $\lim_{k\to 0} S(-2k) = W$.

The Applicant has now found that at least a second order Taylor approximation of S(−2k) can be used to extract geometrical parameters from the radio-frequency dependent backscattered ultrasound data. Surprisingly, the Applicant has found that a second order approximation provides stable and reliable data which follows the experimental data sufficiently well, if not better, compared to higher order approximations. The second order Taylor expansion in k of S(−2k) is of the form:

$$S(-2k) \approx C_0 + (-2k)C_1 + (-2k)^2 C_2. \quad (8)$$

It has been shown above that $C_0 = S(-2k)|_{k=0}$ is the packing factor W. The second constant $C_1$ is necessarily equal to zero because of parity (if the tissue sample is turned around 180 degrees, the tissue properties remain the same). Since S(−2k) is a non dimensional number, the third constant $C_2$ must be a surface. This inference is known in crystallography, using small angle neutron, light, and X-ray scattering to determine polymer and protein radius of gyration. In the Guinier region, $C_2$ is negative and $-C_2$ is related to the square of the radius of gyration ($R_g$) of the clusters of scatterers. Hence, $$S(-2k) \approx W - 4R_g^2 k^2. \quad (9)$$

For identical spherical scatterer sub-units of radius a that form clusters with a gyration radius $R_g$ (that can model individual red blood cells when there is no aggregation), and recombining Equations 2, 5 and 9, the Applicant has found that:

$$BSC(-2k) = \frac{1}{3\pi}HC^2k^4a^3\left[3\frac{\sin(2ka) - 2ka\cos(2ka)}{(2ka)^3}\right]^2 \times [W - 4R_g^2 k^2] \quad (10)$$

Equation 10 can also be expressed as follows:

$$BSC(-2k) = \quad (11)$$
$$\frac{1}{3\pi}HC^2k^4a^3\left[3\frac{\sin(2ka) - 2ka\cos(2ka)}{(2ka)^3}\right]^2 \times [W - 2.4D^2a^2k^2],$$

where D is the gyration diameter of an aggregate (expressed in number of scatterer sub-units e.g. number of red blood cells).

For a suspension of identical weak scatterers such as red blood cells in blood, all the parameters in Equation 11 are known (a, C) or can be easily determined (e.g. H can be determined by micro-centrifugation). A least mean squared polynomial fitting of the frequency dependence of the back scattering coefficient (BSC), by replacing k=2πf/c (c is the speed of sound), directly allows the determination of W and D.

The Applicant has found that this model can be used to achieve data reduction of experimental BSC measures on aggregating red blood cells. By considering an isotropic 3D aggregate of radius R, $R_g$ is related to R by $$R_g = \sqrt{\frac{3}{5}} R.$$

Hence, $$D = \sqrt{\frac{5}{3}} R_g / a,$$

where D is the isotropic diameter of an aggregate (expressed in number of red blood cells). Estimated values of W and D, and their combinations, can be deduced from Equation 11 by least mean squared polynomial fitting of the BSC as a function of frequency. In other words, the spatial organization and cluster size of red blood cells can be estimated from the frequency power spectrum and from the characterization of one red blood cell. This novel approach uses a second order model to acoustically characterize red blood cell aggregation in terms of the aggregate size. For convenience, the Applicant's novel model is referred to herein as the Structure Factor Size Estimator (SFSE) model.

The Applicant has also discovered that a Guinier plot can be used to determine the upper frequency limit of ultrasound for the SFSE model. As far as the Applicant is aware, this is the first time that a Guinier plot has been used in the field of ultrasound. In X-ray and neutron spectroscopy, the Guinier domain is the domain of application of a second order approximation, and it can be estimated using a Guinier plot consisting of plotting $k^2 \to \log S(-2k)$. The quadratic approximation is valid when the slope is linear. Since the model of the present invention is based on a second order approximation of the structure factor, the Guinier plot can be used to determine, as in X-ray and neutron spectroscopy, the upper frequency limit of the domain of application of the model, i.e. when the Guinier plot is linear.

Although the Applicant's SFSE model is based on a system having substantially similar individual scatterers (scatterer sub-units) where the scattering cross-section of a single scatterer is measurable or known and where the scatterers are substantially similar in terms of acoustical impedance and size so that the differences in size between the individual scatterers can be distinguished from clustering scatterers, meaningful qualitative data can still be obtained if this is not the case. For example, the Applicant has found that when the Born approximation does not necessarily apply e.g. when the size of the aggregates is large, the estimated scatterer physical parameters are still meaningful so the system need not be Born approximation.

The SFSE model can be adapted for application to scattered ultrasound measurements. For example, the structure factor reported in Equation 6 can be expressed for scattering at different angles as $S(k,\theta)$. The expression of the angle dependent scattering cross section $\sigma_b(k,\theta)$ is also known. Under the Born approximation (weak scattering), the data reduction model (Equations 5 to 11) presented here can therefore also be applied to scattering at different angles.

The Applicant has also adapted the SFSE model to simultaneously estimate tissue attenuation and physical properties of the scatterers. For convenience, the attenuation model is referred to as the Structure Factor Size and Attenuation Estimator (SFSAE). The SFSAE model comprises fitting the spectrum of the backscattered radio-frequency echoes from blood to an estimated spectrum by a modified model, described below.

Assuming that the Born approximation is valid (weak scattering), the model proposed above (Equation 11) can be modified to predict the theoretical backscatter coefficient from blood in the presence of an intervening attenuation layer using:

$$BSC_{theor}(-2k) = \frac{1}{3\pi}HC^2k^4a^3\left[3\frac{\sin(2ka) - 2ka\cos(2ka)}{(2ka)^3}\right]^2 \times [W - 2.4D^2a^2k^2]A(-2k) \quad (12)$$

where A is the frequency-dependent attenuation function given by:

$$A(-2k) = e^{-4\alpha_0 f^i d} \quad (13)$$

where f is the frequency, i is the power law of the frequency dependence, and $\alpha_0$ is the total attenuation (in dB/MHz) defined by:

$$a_0 = \sum_t a_t e_t,$$

where $\alpha_t$ and $e_t$ are respectively the intervening tissue layer attenuations (in dB/cm/MHz) and thicknesses, and t represents each layer. It is assumed, as a first approximation, that the attenuation increases linearly with the frequency, i.e. that $i=1$: $\alpha(f)=\alpha_0 f$. The method also applies to any value of i.

The backscatter coefficient that can be estimated from experimental measures of radio-frequency ultrasound echoes is given by:

$$BSC_{meas}(-2k) = BSC_{ref}(-2k)\left[\frac{\overline{P_{meas}(-2k)}}{\overline{P_{ref}(-2k)}}\right] \quad (14)$$

where $P_{meas}$ is the backscattered power spectrum obtained by averaging power spectra of several backscattered echoes from blood (typically 400); $BSC_{ref}$ and $\overline{P_{ref}}$ are respectively the reference backscatter coefficient and the mean reference power spectrum obtained from a diluted sample of non-aggregated red blood cells at a low hematocrit (typically H=6% to ensure Rayleigh scattering). In this case, several echoes are also averaged (typically 400). This last blood sample is used to compensate the backscattered power spectrum $\overline{P_{meas}}$ for the electromechanical system response, and the depth-dependent diffraction and focusing effects caused by the ultrasound beam. The reference backscatter coefficient $BSC_{ref}$ can be estimated using the "Rayleigh estimation" approach described in Yu and Cloutier, Journal of the Acoustical Society of America, 122, 645-656 (2007), the contents of which are incorporated herein by reference. The theoretical value is known in the art as the Perkus Yevick packing factor for cylinders (see also Equation 4).

The packing factor W, aggregate diameter D, total attenuation $\alpha_0$ and frequency dependence i along the propagation path are determined by matching the measured backscatter coefficient $BSC_{meas}$ given by Equation 14 with the theoretical $BSC_{theor}$ given by Equation 12. For this purpose, values of W, D, $\alpha_0$ and i are searched minimizing the cost function $F(W, D, \alpha_0, i) = \|BSC_{meas} - BSC_{theor}\|^2$. For the case of a linear frequency dependence (i.e., $i=1$), the cost function is given by $F(W, D, \alpha_0)$. This cost function has one minimum (i.e. one solution), as confirmed by plotting the cost function surface $F(W, D)$ with varying values of $\alpha_0$ for several experimental conditions.

It should be appreciated that any other parameters can be fixed and the others minimized, other than the parameters discussed above. With the SFSAE model, four parameters (W, D, $\alpha_0$, i) are simultaneously determined but other parameters could also be simultaneously estimated. For example, in the case of blood, the hematocrit H is a quantity that affects the frequency dependence of the backscatter coefficient that could advantageously be determined non-invasively (five parameters are then estimated: W, D, $\alpha_0$, i and H). For other applications, any of the physical parameters described in Equations 12-14 (e.g., the impedance mismatch C that depends on the density and compressibility of blood cells and plasma, the particle volume Vs, the pair correlation g(r)) could be unknown and simultaneously determined through the minimization equation $\|BSC_{meas} - BSC_{theor}\|^2$.

BRIEF DESCRIPTION OF THE DRAWINGS

Further aspects and advantages of the present invention will become better understood with reference to the description in association with the following in which:

FIG. 3(a) is a graph from Example 1 of the backscatter coefficient for a 6% hematocrit non-aggregating suspension of red blood cells (H6) and a 6% hematocrit aggregating whole blood (T6) sheared at 100 s$^{-1}$ plotted with the theoretical Rayleigh prediction (Equation 1), a $2^{nd}$ order Taylor model (SFSE model) of an embodiment of FIG. 2 with W=0.6 and D=0.8 (Equation 11), and previously obtained H6 experimental data;

FIG. 3(b) is a graph from Example 1 of the backscatter coefficient for a 40% hematocrit non-aggregating suspension of red blood cells (H40) sheared at 50 s$^{-1}$ and a 40% hematocrit aggregating whole blood (T40) sheared at 100 s$^{-1}$ plotted with the theoretical Rayleigh prediction with W=0.04 and W=0.11, and the SFSE model with W=0.1 and D=0.5;

FIGS. 4(a) and (b) are graphs from Example 1 illustrating the backscattered coefficient (BSC) during the kinetics of red blood cell aggregation for (a) T6 and (b) T40 blood at residual shear rates of 0, 2, 10 and 30 s$^1$ at three different frequencies;

FIGS. 7(a)-(d) each show represented gray scale images, binary images and segmented microscope images at (a) t=0 s, (b) t=15 s, (c) t=60 s, and (d) t=165 s during the kinetics of red blood cell aggregation of a T6 sample of Example 1;

FIGS. 8(a)-(d) are histograms from Example 1 of the red blood cell aggregate dimension determined optically from FIGS. 7(a)-(d) in number of cells at time 0, 15, 60 and 165 s, respectively;

FIG. 9 is a graph from Example 1 comparing estimated D values obtained with an optical method and an ultrasound method according to an embodiment of FIG. 2;

FIGS. 14(a)-(d) illustrate parametrical images of FIG. 13 illustrating BSC, spectral slope (SS), packing factor (W), and diameter (D), respectively;

FIG. 15 is an enlarged image of FIG. 14(d) showing regions 1, 2 and 3 from where measurements were taken;

FIG. 16 is a table showing the values of BSC, SS, W and D for the regions 1, 2 and 3 of FIG. 15;

FIG. 17 illustrates a Couette device experiment of Example 3;

FIG. 18 illustrates a tube experiment set up of Example 3;

FIG. 21 illustrates a graph from Example 3 of backscatter coefficients for blood sheared at different residual shear rates (5, 10, 20, 30 and 50 s$^{-1}$) and measured with a non-attenuating phantom, and corresponding fitting with the SFSE model with compensation for blood attenuation;

FIGS. 22(a)-(b) illustrate backscatter coefficients for blood sheared, in Example 3, at (a) 10 s$^{-1}$ and (b) 50 s$^{-1}$ and measured with five attenuation phantoms, with $\alpha_0$ varying between 0.013-0.448 dB/MHz, and fitted with the SFSE model for a non-attenuating phantom, and the SFSAE model for four attenuating phantoms;

DETAILED DESCRIPTION OF THE INVENTION

A system 10 and a method 12 for characterizing ultrasound scatterers in a medium, according to an embodiment of the invention, is described below. Broadly, the system 10 comprises a transmitter for transmitting an ultrasound signal to a region of interest, a detector for detecting a scattered or a backscattered ultrasound signal; and a processor for processing the detected ultrasound signal including applying an embodiment of the method of the invention to estimate a physical parameter of scatterers in the region of interest. Specifically, the region of interest comprises a plurality of scatterers in a medium, the plurality or scatterers including clusters of scatterer sub-units, the scatterers or scatterer clusters having a physical property value to be estimated.

In the embodiments of the system 10 and method 12 described below, the scatterer sub-units are red blood cells suspended in blood plasma and the scatterers include red blood cell clusters and red blood cells. Absolute values of physical properties of the scatterers are estimated by backscattered ultrasound signals. Specifically, these are a mean packing factor, W, and a mean diameter, D, of the scatterers which can be useful for monitoring, in vivo, the aggregation or disaggregation of the red blood cells in real-time. However, it should be understood that the system 10 and the method 12 of the invention can equally be applied to any other cells in blood as well as to any other suspensions and emulsions other than blood, and to scatterers in a solid medium.

Figure 1:
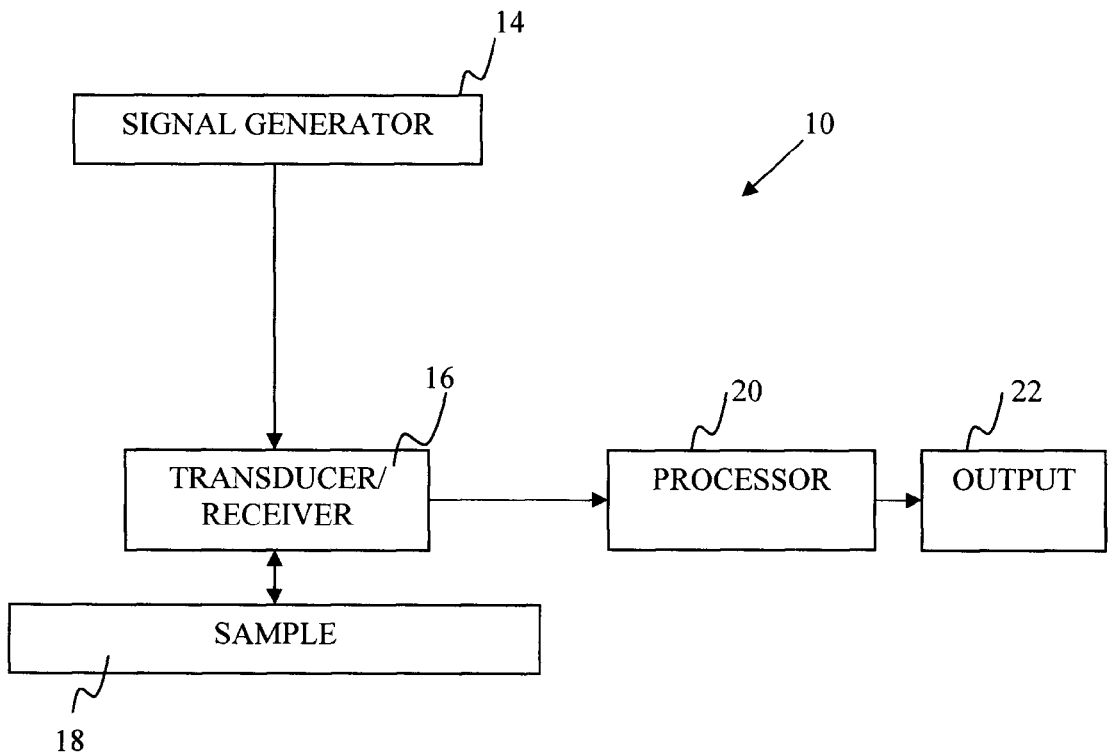
FIG. 1 is a schematic block diagram of an embodiment of a system according to the present invention.

An overview of the embodiment of the system 10 is shown in FIG. 1. The transmitter and detector comprise a signal generator 14 or pulser and a transducer/receiver 16. Alternatively, signal generator 14 and the transducer/receiver 16 can be incorporated in a single device. The signal generator 14 generates an electrical signal which is transmitted to a transducer 16. The transducer 16 converts the electric signal into an acoustic input signal that is introduced into a sample 18. The same transducer/receiver 16 acts as a sensor to sense or detect at least a portion of the acoustic energy that is scattered by the sample in response to their interaction with the acoustic input signal and provide an output signal to the processor 20. The processor 20 processes the output signal to provide an output 22 which is at least one physical parameter value of scatterers, in this embodiment, a mean normalized dimension (e.g. diameter D) of the scatterers as well as a packing factor (packing factor W) of scatterers in the blood.

Alternatively, the system 10 may include one or several separate transducers/probes as a receiver or receivers (not shown). In this case, one transducer transmits echoes and the other receives echoes. This can allow the dependence of the mean normalized dimension on the insonification angle to be assessed for measuring the anisotropic structure of the scatterers.

The sample 18 comprises individual red blood cells and/or clusters of red blood cells in blood. As the present embodiment of the system 10 relates to an in vivo estimation of the physical parameter of clustered red blood cells, the sample 18 is a blood vessel of a patient which can be considered as a 'live' vessel. The transducer/receiver 16 is positioned on the skin of the patient over a blood vessel lying underneath the skin. This can provide real-time information on the red blood cell aggregation or disaggregation of the patient. In an alternative embodiment, the system 10 and the method 12 of the invention can be applied to obtain an in vitro physical parameter estimation. In that case and for assessing red blood cell aggregation in blood, a blood sample is taken from a patient and the transducer 16 is positioned on a wall of a container containing the sample and the sample agitated to avoid sedimentation. It will be appreciated that the sample can therefore be in any form in which an ultrasound signal can be transmitted to scatterers in the sample.

Considering now the individual components of FIG. 1 in more detail, the signal generator 14 is a monocycle generator capable of producing a single cycle of radio-frequency signals at pre-settable pulse frequencies, or any other suitable signal generator. For measuring red blood cells in blood, the frequency is set within the range of 1 MHz to 100 MHz typically and a pulse repetition rate between 500 Hz and 5 kHz is used. A commercially available monocycle generator can be used such as Avtech pulse generator (model AVB2-TA-C-CRIMA, Ottawa, Canada).

The transducer 16 can be any type of broadband ultrasound transducer such as V313-SM or V317-SM (Panametrics, MA, USA) or PVDF (VisualSonics, Toronto, Canada). In this embodiment, a PVDF transducer having a frequency range of 25-50 MHz, a transducer radius of 3 mm and a focal length of 6 mm is used to acquire and store one hundred radio-frequency lines. Any wide band transducer or probe such as, for example, RMV710 (VisualSonics, Toronto, Canada) with a centre frequency of 25 MHz, a focal distance of 1.5 cm and a F-number of 2.1 can also be used. The transducer 16 includes a receiver portion which receives the backscattered ultrasound signals and transmits them to a signal processor 20.

For detecting red blood cells in blood, the transducer 16 may have a centre frequency of 25 MHz, and preferably be within the range of 10-40 MHz. The operating frequency is chosen as a function of the measurement contemplated. Therefore, in alternative embodiments where the system 10 and the method 12 of the invention are applied to other particle suspensions or weak scatterers in a homogenous medium, transducers with a lower or a higher frequency range can be used, for example transducers having frequencies below 1 MHz and above 100 MHz. Multiple transducers can also be used. The relationship between frequency, relative wavelength and scatterer size (ka) is known and appropriate frequencies can be selected on this basis.

The processor 20 includes an amplifier for amplifying the signal and a converter for converting the analogue signal to a digital signal. In this embodiment, commercially available diplexers, amplifiers and converters are used such as Ritec diplexer (model RDX-6, Warwick, R.I., USA), a 10 dB Mitec linear amplifier (model AU-A3-0120, Hauppauge, N.Y., USA), and an 8 bits 500 MHz sampling frequency GageScope acquisition board (model 8500CS, Montreal, Canada).

Further processing of the digital signal is either performed by the processor 20, or another processor (not shown) such as a computer or any other digital signal processor. The further processing may include normalizing the digital signal, conversion of the digital signal to ultrasound data representing a power spectrum, and application of an embodiment of the method 12 of the present invention to estimate diameter D and packing factor W of the red blood cell clusters. The processor may also include a memory for storing the digital signal, storing instructions for the data processing, and storing the output data 22 of the data processing. The system 10 may include a display (not shown) for displaying the output data 22, the power spectrum or the digital signal.

The processor 20 may include an oscilloscope which converts the ultrasound digital signal and displays the processed output signal (e.g. as a power spectrum), linked to a further processor for estimating the physical parameter values of the red blood cell clusters.

The system 10 may be contained within a single housing to form a single apparatus or device comprising separate parts. Single housing embodiments may be suitable for bedside or self-monitoring applications, for example. Such an apparatus may also be applied to in vitro particle characterization methods for applications where sampling is preferable.

Finally, the system 10 may comprise an alarm or alert device (not shown) coupled to the processor 20 for indicating if and when the estimated physical parameters match, come close to, fall below or exceed a pre-defined limit or range. For example, in the case of red blood cell aggregation, the alarm can be activated automatically if the detected aggregated size comes close to, reaches or exceeds a predefined dangerous aggregate size. This in turn may activate an automatic administration of drugs or other therapy or treatment.

Figure 2:
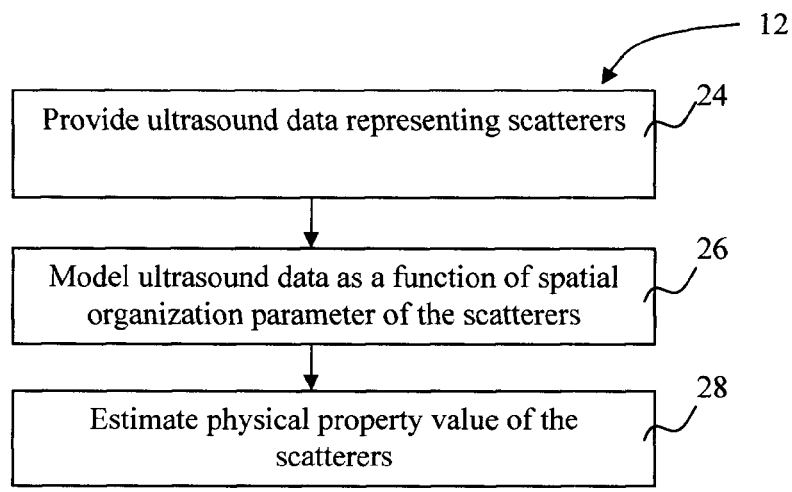
FIG. 2 is a flow diagram illustrating an embodiment of a method of the present invention.

FIG. 2 illustrates an overview of a first embodiment of the method 12 of the present invention, for incorporation in the embodiment of the system 10 described above, for example. However, it will be appreciated that the method 12 can be used in different systems and for other applications. Broadly, this embodiment of the method 12 commences at Step 24 by providing ultrasound data representing scatterers. In Step 26, the ultrasound data is modelled based on an at least second order function of a spatial organization parameter. In Step 28, a physical parameter value of the scatterers is estimated based on the modelled data using a parameter estimation algorithm.

Specifically, in Step 24, the ultrasound data represents an ultrasound power spectrum of a region of interest comprising a plurality of scatterers in a medium, the plurality of scatterers including clusters of scatterer sub-units as well as individual scatterer sub-units. In this embodiment, the scatterer sub-units are red blood cells and the medium is blood. The scatterers have a physical property value to be estimated, which in this case is the average scatterer diameter D and the scatterer packing factor W. At least one physical parameter value of the red blood cells is known. Providing the ultrasound data includes positioning the transducer 16 adjacent to the sample 18 and the signal generator 14 generating electric signals which in turn excite the transducer 16 to produce ultrasonic signals which are transmitted to the sample 18. In this embodiment, the transducer is placed adjacent a skin of a patient close to a blood vessel lying underneath the skin. The backscattered signal is detected and acquired by the transducer 16 and forwarded to the processor 20 which processes the received backscattered signals to obtain the frequency dependent backscatter coefficient (BSC) by normalization. The backscattered data is acquired as one hundred radio-frequency lines and stored in a memory of the processor 20, or another memory, as a spectrum. In this embodiment, a plurality of spectra are obtained then averaged to provide a mean spectrum to reduce noise. Ten spectra are averaged although the invention is not limited to this number or to the use of a mean spectrum if a single spectrum is not too noisy. A window of typically 1024 points is selected in each line in the focal zone of the transducer and the data in the selected window Fourier transformed. The amplitude is then squared to obtain the power spectrum P of the backscattered signal.

The power spectrum P is then 'normalized' to remove any signals due to the acquisition apparatus itself as it is known that measured backscattered data contain artefacts due to the ultrasound signal acquisition apparatus. This is achieved by determining the artefact signal associated with the apparatus itself and subtracting this from the data acquired by that apparatus to obtain the true ultrasound 'signature' of the sample being measured to obtain the backscatter coefficient (BSC). It will be appreciated that the artefact element will only need to be determined once for a specific apparatus or system. There are a number of known methods for normalizing such data which can be used, for example, the method described in Wang, S. H. and Shung, K. K., "An approach for measuring ultrasonic backscattering from biological tissues with focused transducers," IEEE Transactions on Biomedical Engineering 44(7), 549-554 (1997), or blind deconvolution or substitution methods (hereinafter referred to as "Wang and Shung").

In this embodiment, calculation of the backscattered coefficient comprises two stages. In a first stage, a 6% hematocrit reference medium (non-aggregated red blood cells) is prepared by obtaining a sample of blood from the patient and anti-coagulating this sample with 3 g/L of ethylene diamine tetra acetic acid (EDTA). The buffy coat is removed after centrifugation at 2000×g (g is the gravitational force) and a 60 mL sample is prepared with a hematocrit suspension volume density of 6% and a suspending medium of isotonic saline water. Ultrasound measurements of the 6% hematocrit sample are taken whilst stirring with a magnetic agitator to avoid sedimentation. The measurements are then repeated on a stainless steel plane reflector submerged in degasified water and positioned in the focal plane of the transducer/receiver 16. A window of typically 1024 points in each line is selected in the focal zone of the transducer 16 and Fourier transformed; the amplitude is squared to get the power spectrum P of the backscattered signal. These data are then averaged over several acquisitions (100 here) to provide $\overline{P_{H6B}}$ and $\overline{P_{plane}}$, where subscripts B and plane mean "beaker" and "planar reflector", respectively. The absolute backscatter $BSC_{H6}$ of Rayleigh diffusers at the focal plane of each focused transducer is measured by the substitution method with diffraction and attenuation compensations:

$$BSC_{H6} = \frac{\overline{P_{H6B}(f,F)}}{\overline{P_{plane}(f,F)}} \times \frac{R_p^2 k^2 r^2}{8\pi d\left[1+\left(\frac{kr^2}{4F}\right)^2\right]} \times e^{(4\alpha_{H6}d)}, \qquad (15)$$

where $R_p$, k, r, d, F and $\alpha_{H6}$ are, respectively, the reflection coefficient of the planar reflector (assumed to 1), the wave vector, the transducer radius, the inspected depth, the transducer focal length, and the H6 attenuation coefficient. This method is described, for example, in Ueda, M. and Ozawa, Y, "Spectral analysis of echoes for backscattering coefficient measurement," Journal of the Acoustical Society of America 77(1), 38-47 (1985).

In a second stage, the 6% hematocrit sample is introduced and sheared in a Couette flow system where the ultrasound measurements are performed using the transducer/receiver 16, Fourier transformed and the amplitude squared to provides its power spectrum $P_{H6}$. Then the blood sample is introduced, sheared and insonified in the Couette device and its power spectrum $P_{Blood}$ is calculated similarly. The backscatter coefficient is then computed using the modified substitution method of "Wang and Shung".

$$BSC_{Blood} = BSC_{H6} \times \frac{\overline{P_{Blood}}}{P_{H6}} \times e^{4d(\alpha_{Blood}-\alpha_{H6})} \qquad (16)$$

where $BSC_{H6}$ is given by Equation 15 and $\alpha_{Blood}$ is the attenuation coefficient of the investigated samples. Values of $\alpha_{H6} \approx \alpha_{T6} = 0.03$ dB/cm/MHz, and $\alpha_{H40} \approx \alpha_{T40} = 0.22$ dB/cm/MHz were selected from published data for all shear rates. Note that in this case a 6% hematocrit was used but any other characterizable scatterer suspension could also be used.

In step 26, the ultrasound data is modelled as a function of a second order spatial organization parameter defining the spatial organization of the scatterers, and in step 28, the physical property values of D and W of the scatterers are estimated from a frequency function based on a polynomial fitting. This is according to the SFSE model developed by the Applicant.

The normalized ultrasound data is modelled based on a Structure Factor and the Born approximation, and the physical property values of D and W estimated by a second order polynomial fitting (in this embodiment, a Taylor approximation) of the measured ultrasound data. In practice, this is achieved by the application of Equation 10 or 11, derived by the Applicant. Equation 10 is repeated below for completeness:

$$BSC(-2k) = \frac{1}{3\pi} HC^2 k^4 a^3 \left[3\frac{\sin(2ka)-2ka\cos(2ka)}{(2ka)^3}\right]^2 \times [W-4R_g^2 k^2] \qquad (10)$$

As will be appreciated, parameters H (the hematocrit), C (the acoustical relative impedance mismatch between the red blood cells and their suspending medium (saline or blood plasma)), k (ultrasound wave vector), and a (the mean radius of individual scatterers or red blood cells) must be determined or estimated before polynomial fitting of the measured backscatter coefficient (BSC) using Equation 10. For red blood cells, these can be obtained from published data on blood values or estimated using microscopy of diluted blood, for example. In the case that the present application is applied to particle suspensions other than red blood cell units in blood, the parameters H, C, k and a must be determined or estimated before polynomial fitting of the normalized BSC using Equation 10. The validation of the theory implemented in the present invention is provided in Example 1 and some results from this embodiment of the method in Example 2.

Additional method steps (not shown) may include displaying the estimated physical parameter values, and activating an alert if the estimated values match, approach or fall within or outside of predefined values or limits.

A further additional method step may include compensating for the attenuation of intervening material between the scatterers being detected and the ultrasound transducer.

In a second embodiment of the method 12, Steps 26 and 28 are adapted to estimate the attenuation of biological tissue, and/or other material intervening between the transducer/receiver 16 and scatterers, at the same time as estimating the physical parameter values of the scatterers. The attenuation is estimated simultaneously with structure properties (W and D) according to the SFSAE model developed by the Applicant.

Figures 20A, 20B:
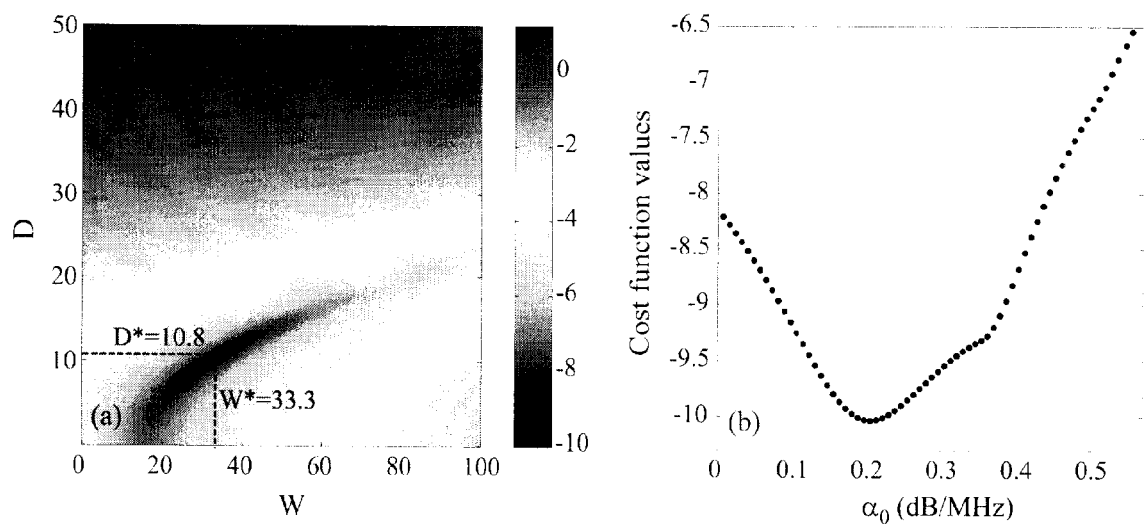
FIGS. 20(a)-(b) illustrate (a) a single minimum (W*, D*) of a cost function F(W,D,$\alpha_0$) for a fixed value of $\alpha_0$, and (b) a single minimum of a cost function F(W*, D*,$\alpha_0$) for varying values of $\alpha_0$. of Example 3.

This second embodiment differs from the previous embodiment of the method 12 in that once the frequency dependent backscatter coefficient ($BSC_{meas}$) of the sample has been normalized, the measured backscatter coefficient $BSC_{meas}$ is compared with the theoretical $BSC_{theor}$ given by Equation 12, to determine the packing factor W, aggregate diameter D and a total attenuation $\alpha_0$ of intervening material between the transducer/receiver and the scatterers. For this purpose, values of W, D and $\alpha_0$ are searched minimizing the cost function $F(W, D, \alpha_0)=\|BSC_{meas}-BSC_{theor}\|^2$. This cost function has one minimum (i.e. one solution), as confirmed by plotting the cost function surface F(W, D) with varying values of $\alpha_0$ for several experimental conditions (see FIG. 20 of Example 4, for example). In this way, W, D and $\alpha_0$ are simultaneously estimated from a single acquisition step of backscattered echoes. The total attenuation $\alpha_0$ of intervening tissue layers between the probe and the scatterers are taken into account and estimated on an individual basis without the necessity to know or measure any other a priori parameters (i.e., attenuation, speed of sound, tissue thickness, tissue composition, etc.).

In another aspect of the method 12, a physical parameter value (e.g. size) of a cluster of scatterers is estimated using a Guinier plot determined from the backscattered signal from blood, or any other medium, through the direct application of X-ray and neutron spectroscopy methodologies on S(-2k). The Guinier plot consists of plotting $k^2 \rightarrow \log S(-2k)$. The slope scales as $R_g^2/3$ and therefore allows an estimation of the radius of gyration ($R_g$) and diameter D of the scatterers $$\left(D = \sqrt{\frac{5}{3}} R_g/a\right)$$

Figure 12:
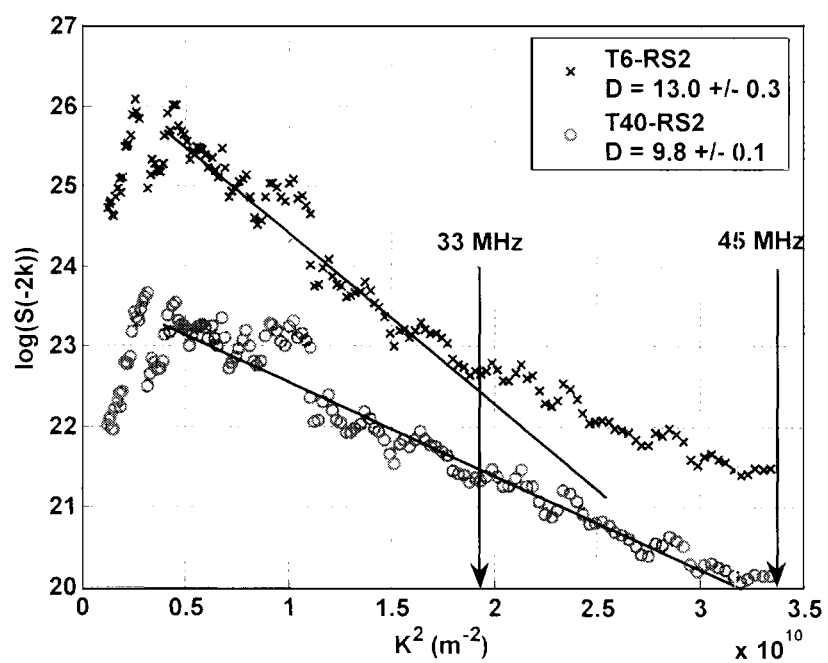
FIG. 12 is a graph illustrating Guinier plots of T6 and T40 blood samples submitted to a residual shear of 2 s$^{-1}$ with the cluster sizes D estimated using the Guinier plot reported in the legend.

(see FIG. 12 where D values are estimated from the linear slope of the Guinier plots).

In a further embodiment of the method 12, anisotropic clustering scatterers are characterized using a backscattered ultrasound signal. In this embodiment, the ultrasound data comprises pulse echo backscattering measurements from different angles (using one mobile transducer or many transducers positioned at different angles). These measurements are integrated and angle dependent estimations of W and D using Equation 11 for each orientation are calculated to provide a means to determine the mean geometrical shape of the clustered particles. Similarly, anisotropic measurements can be fitted to the Applicant's SFSAE model to obtain, with Equation 12, W, D, $\alpha_0$, i or any other sets of physical parameters describing the scatterers.

In a yet further embodiment of the method 12, anisotropic clustering scatterers in a medium are characterized using non backscattered signals. In this aspect, a system of multiple transducer/receivers (a minimum of two) are used. At least one transmitter (E) emits an ultrasound pulse into an area of interest. The angle dependent scattered waves are recorded at different angles using one transducer (R) at different positions, or a system of multiple transducers (R). Under the Born approximation (weak scattering), the angle dependent scattered signals are processed using angle dependent $S(k,\theta)$, $\sigma_b(k,\theta)$ and the Applicant's novel SFSE model (Eqs. 5 to 11). Similarly, with the SFSAE model, the angle dependent scattered signals are processed using angle dependent $S(k,\theta)$, $\sigma_b(k,\theta)$ and $A(k,\theta)$.

Example 1

This Example Illustrates a Validation of the First Embodiment of the Method 12

Summary:

Different samples of whole blood and red blood cell suspensions at 6% and 40% hematocrits were prepared and quantitatively characterized at room temperature using three focused wideband transducers covering the bandwidth from 9 to 30 MHz. According to the first embodiment of the present invention, a second order Taylor approximation of the structure factor was used to achieve data reduction of the BSC measurements, to extract two physical parameters, the packing factor (W) and the mean normalized dimension of isotropic aggregates (D). The D parameter was validated by an optical imaging method at 6% hematocrit under static conditions. Both parameters closely matched theoretical values for non-aggregated red blood cells. This therefore validated the theoretical SFSE model of the present invention.

Blood Preparation:

Fresh porcine whole blood was anti-coagulated with 3 g/L of ethylene diamine tetra acetic acid (EDTA). The buffy coat was removed after centrifugation at 2000×g and four 60 mL samples were prepared. The first sample (H6) had a hematocrit (volume density) of 6% and the suspending medium was isotonic saline. The second sample (T6) had a hematocrit of 6% and the suspending medium was porcine blood plasma. The third sample (H40) had a hematocrit of 40% and the suspending medium was isotonic saline. Finally, the fourth sample (T40) had a hematocrit of 40% and the suspending medium was porcine plasma. These samples were sheared in a Couette flow system where the ultrasound measurements were performed in a manner substantially as described for the first embodiment of the method 12.

Ultrasound and Normalization:

The 6% hematocrit reference to be used for assessing the backscattering coefficients of blood with the Couette device, was determined in a manner substantially as described for the first embodiment of the method 12. Normalization differed from that described for the first embodiment in that three broadband transducers were used: V313-SM (Panametrics, USA) with a centre frequency of 15 MHz, a −3 dB bandwidth of 9-14 MHz, a transducer radius of 4.5 mm and a focal length of 12 mm; V317-SM (Panametrics, USA) with a centre frequency of 20 MHz, a −3 dB bandwidth of 15-26 MHz, a transducer radius of 4.5 mm and a focal length of 12 mm; and PVDF (#054-40-6) (VisualSonics, Canada) with a centre frequency of 35 MHz, a −3 dB bandwidth of 26-40 MHz, a transducer radius of 1.5 mm and a focal length of 6 mm. The 15 MHz transducer was excited at a lower frequency to cover a different frequency band than the MHz transducer. The pulse-echo acquisition system was composed of a pulse generator (Avtech AVB2-TA-C-CRIMA, CANADA), a diplexer (Ritec model RDX-6, USA), a 10 dB linear amplifier (Mitec model AU-A3-0120, USA), a pulser-receiver that was used as a wideband receiver (Panametric model 5900 PR, Waltham, Mass., USA), and an 8 bits 500 MHz sampling frequency GageScope acquisition board (model 8500CS, CANADA).

Following the beaker and plane reflector measurements, each transducer was then successively placed in the Couette device with its focal plane matching the centre of the 2 mm gap between both concentric cylinders filled with blood. An agar gel was used to fill the hole that was made to position the transducer within the static cylinder; the solidified gel was cut to match the curvature of the cylinder in order to minimize any flow disturbance. The non-aggregating H6 sample was filled and sheared at 50 s$^{-1}$ while acquiring 100 radio-frequency lines for each transducer. The shear rate was precisely controlled by the rotation speed of the moving Couette cylinder. The H6 data provided $P_{H6}$ for the modified substitution method described above in Equation 16. Following these measures, the H6 sample was removed and the Couette device was washed with saline. H40 was then introduced and rotated at the same shear rate of 50 s$^{-1}$ in the Couette device. $BSC_{H40}$ was computed also using Equation 16 (with $\overline{P}_{Blood} = \overline{P}_{H40}$) to provide comparison data for non-aggregating conditions at 40% hematocrit.

Then, T6 and T40 blood samples were successively introduced in the Couette device. For each aggregation kinetic experiment, the blood was first sheared at 100 s$^{-1}$ for 2 minutes to disrupt red blood cell rouleaux. The shear rate was then changed to residual values of 0, 2, and 30 s$^{-1}$ for 3 minutes. During each experiment, 20 radio-frequency lines were acquired every 2 s for 190 s, starting 10 s before the application of the residual shear. At each time instant, a power spectrum was averaged over 20 radio-frequency lines to obtain $\overline{P}_{Blood}$ in Equation 16. The BSC of H6, H40, T6 and T40 samples, sheared in the Couette device, were computed using Equation 16. Finally, since suspended red blood cells are Rayleigh scatterers in the range of frequencies considered here, theoretical values of $BSC_{H6}$ and $BSC_{H40}$ were also computed using Equations 1, 2 and 4. This second approach was used to confirm the experimental Couette flow measures of BSC. They are identified as "Rayleigh estimations" in FIG. 3.

Microscopy Analysis:

Aggregation kinetics of whole blood at 6% hematocrit (T6 sample) under static conditions were also quantified using an optical method on a sample drop of blood. Gray scale images were taken at an optical magnification of 40× (1 pixel=0.6× 0.6 μm) at intervals of 15 s during 3 minutes. This procedure was repeated 3 times with the same blood sample. A 1-16 non aggregating suspension was also imaged for comparison. The images were processed offline to determine the size of each aggregate. The same algorithm was used on all images. First, a segmentation threshold was determined using images normalized in intensity between [0, 1]. The threshold minimized the intra-class variance of the black and white pixels by using the Otsu method (Matlab function "Graythresh", version 7.0.1.24704, Natick, Mass., USA). From the binary images obtained by thresholding, all elements smaller than 7 pixels in diameter were eliminated since they were smaller than a single red blood cell (a typical single red blood cell had a diameter of 12 pixels). The size of each cluster of aggregates was normalized by a 12 pixels diameter circular prototype to obtain the number of red blood cells per aggregate. Following this pre-processing, the histogram of the number of red blood cells per aggregate was traced and fitted to an exponential distribution of mean b, the mean number of red blood cells per aggregate. Assuming isotropic 2D circular aggregates, an optical equivalent of parameter D, given above after Equation 11, was given by:

$$D_{OPT} = \sqrt{\frac{4}{\pi}b}. \tag{17}$$

As a first approximation, the surface occupied by b red blood cells=$\pi(D_{OPT}/2)^2$.

Ultrasonic Characterization of Red Blood Cell Suspensions:

FIG. 3(a) shows BSC obtained with the three transducers on H6, the 6% hematocrit red blood cell suspension reference medium (Equation 15). The BSC on T6 computed with Equation 16 at 100 s$^{-1}$ (T6-RS100, where RS means "residual shear") is also presented. The fitted Taylor model expansion of the present invention (Equation 11) and the theoretical Rayleigh estimation (Equation 1) are also represented, along with published experimental results from Maruvada, S. et al "High-frequency backscatter and attenuation measurements of porcine erythrocyte suspensions between 30-90 MHz," Ultrasound in Medicine & Biology 28(8), 1081-1088 (2002) and "Wang and Shung". FIG. 3(b) shows BSC obtained on H40, the theoretical Rayleigh BSC with W=0.04 and W=0.11 (Equations 1, 2 and 4) and the Taylor model. Values of W obtained with the Taylor model for suspended non-aggregating red blood cells at 6% and 40% hematocrits are very close to the theoretical Perkus Yevick predictions (see Table I). In addition, the estimated value of D=0.78±0.09 for H6 is very close to the expected result of 1 red blood cell/aggregate. Table I illustrates the experimental and theoretical values of W and D for disaggregated red blood cells suspended in an isotonic saline solution at 6% and 40% hematocrits. $W_{PYs}$ and $W_{PYc}$ were calculated using Equations 3 and 4, respectively.

TABLE I

Experimental and theoretical predictions of W and D for H6 and H40

| | H6 | | H40 | |
|---|---|---|---|---|
| | W | D | W | D |
| Experimental values | 0.60 ± 0.03 | 0.78 ± 0.09 | 0.10 ± 0.01 | 0.5 ± 0.1 |
| $W_{PYs}$ | 0.62 | — | 0.04 | — |
| $W_{PYc}$ | 0.74 | — | 0.11 | — |

Kinetics of Red Blood Cell Aggregation:

FIG. 4 illustrates the mean BSC over the respective transducers' bandwidth during the kinetics of rouleaux formation for (a) T6 and (b) T40 blood samples. A high shear rate of 100 s$^{-1}$ had been first applied during the first 10 s (before t=0 s). BSC was taken as the mean value over the transducer bandwidth and the results are expressed as means±one standard deviation over three experiments. At both studied hematocrits, the rouleaux formation kinetic profiles had similar shapes. For instance, at all frequencies, BSC first had a low value, when blood was sheared at 100 s$^{-1}$, which corresponds to the disaggregated state. BSC then gradually increased and stabilized at different levels depending on the applied residual shear rates and on the ultrasound frequency. The highest BSC levels were achieved at a residual shear rate of 2 s$^{-1}$ for all experiments (RS2 curves). As expected, higher shearing (RS10 and RS30) partially disrupted red blood cell aggregates and smaller BSC were thus obtained. Under static conditions (RS0) and for all transducers, the BSC reached an intermediate level near that of RS10. For T40, faster kinetics were observed in the first few seconds at increasing frequencies.

Figure 5:
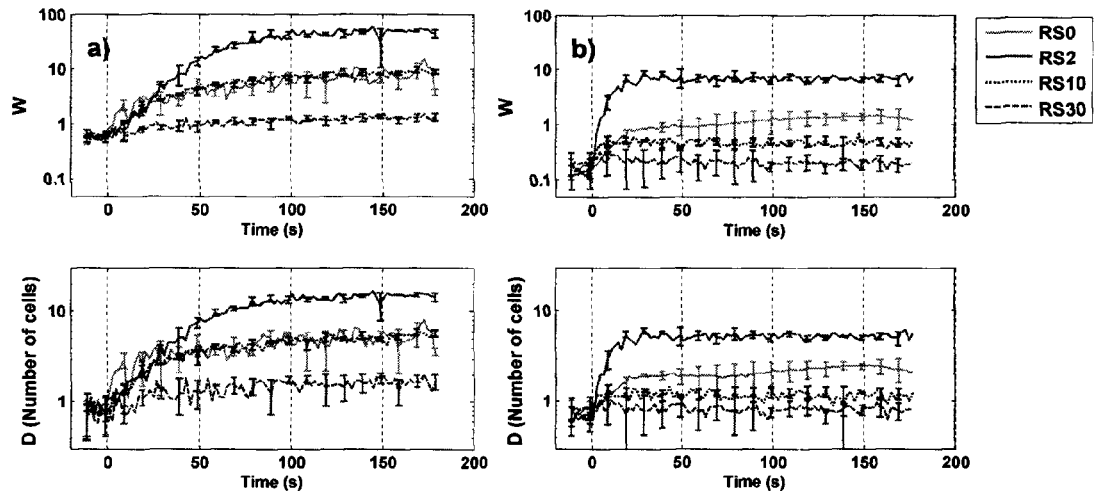
FIGS. 5(a) and (b) are graphs from Example 1 illustrating time variations of fitted parameters W and D during the kinetics of red blood cell aggregation for (a) T6 and (b) T40 blood at residual shear rates of 0, 2, 10 and 30 s$^{-1}$.

FIG. 5 illustrates the evolution of parameters W and D during the process of aggregate formation. A high shear of 100 s$^{-1}$ had been applied during the first 10 s of each acquisition. Results are expressed as means±one standard deviation over three experiments. As seen, W and D increased as a function of time for residual shear rates promoting red blood cell aggregation. The comparison of results at both hematocrits suggests that aggregates formed at 40% hematocrit are smaller in size than those obtained at 6% hematocrit, at each respective residual shear rate. Mean values at the plateau of the kinetic curves for all applied shear rates are summarized in Table II.

TABLE II

T6 and T40 blood fitting parameters W and D at different residual shear rates (averaged values were computed between t = 170 s and 180 s in FIG. 5). RS100 data were averaged between t = 0 s and 10 s. Results are expressed as means ± one standard deviation over three experiments

| Residual | T6 | | T40 | |
|---|---|---|---|---|
| shear rate | W | D | W | D |
| RS0   | 6.8 ± 2.4  | 4.9 ± 1.4  | 1.4 ± 0.1  | 2.4 ± 0.1 |
| RS2   | 48.9 ± 5.7 | 15.0 ± 1.0 | 6.8 ± 1.1  | 5.3 ± 0.6 |
| RS10  | 8.4 ± 0.7  | 5.3 ± 0.4  | 0.5 ± 0.1  | 1.1 ± 0.1 |
| RS30  | 1.3 ± 0.2  | 1.6 ± 0.3  | 0.2 ± 0.1  | 0.7 ± 0.1 |
| RS100 | 0.60 ± 0.09 | 0.87 ± 0.27 | 0.2 ± 0.03 | 0.8 ± 0.1 |

Figure 6:
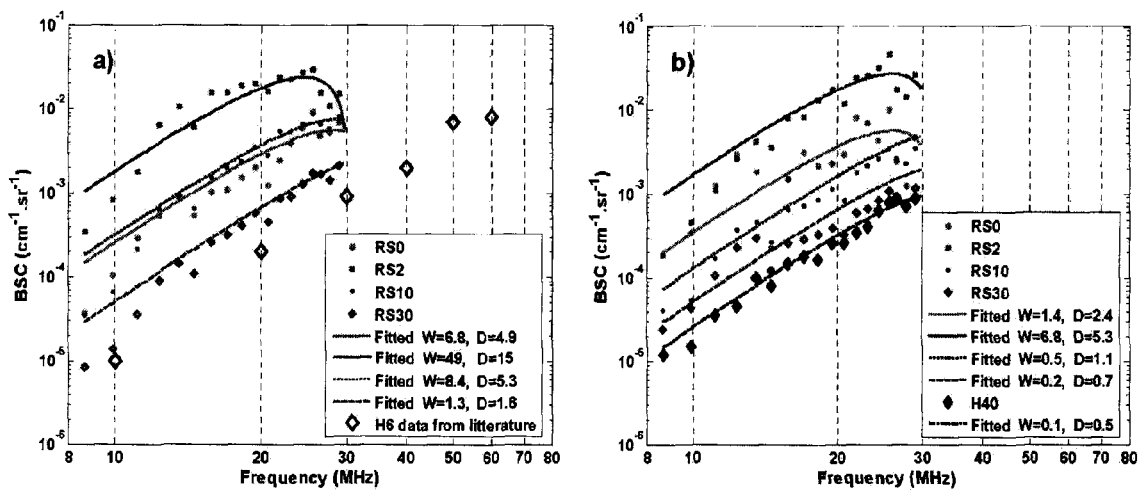
FIGS. 6(a) and (b) are graphs from Example 1 illustrating the frequency dependencies of (a) T6 and (b) T40 blood sheared at residual shear rates of 0, 2, 10 and 30 s$^{-1}$, and corresponding fitted models together with previous H6 experimental data.

Frequency Dependence of the BSC:

FIG. 6 shows BSC as a function of frequency for different residual shear rates and at the plateau of the kinetics of aggregation (temporal means between t=170 s and t=180 s in FIG. 4). H6 experimental data taken from Maruvada, S., Shung, K. K., and Wang, S., "High-frequency backscatterer and attenuation measurements of porcine erythrocyte suspensions between 30-90 MHz," Ultrasound in Medicine & Biology 28(8), 1081-1088 (2002) and "Wang and Shung" are also displayed. Standard deviations are not shown for clarity. It can be seen that BSC increases with the level of aggregation promoted by different residual shears. The BSC is Rayleigh at low frequencies and high shear rates, and becomes non Rayleigh (drop in Spectral Slope SS) with decreasing residual shear RS. Also represented in FIG. 6 are fitted curves based on the SFSE model.

Comparison of Ultrasound and Optical Methods:

FIGS. 7(a)-(d) show typical microscopic images during the aggregation kinetics promoted by Brownian motion. In columns are represented typical microscopic images and image processing at a particular time during the kinetics of aggregation of a T6 sample. The actual treated images were bigger, only the central 300×400 pixels of the whole 960×1280 pixels are shown on FIG. 7. Binary thresholded images are presented in the second row. Segmented objects are given in the third row. Resolution is 1 pixel=0.6 μm×0.6 μm. Histograms of the number of red blood cells per aggregate, arbitrarily partitioned in 15 logarithmically spaced bins, are displayed in FIG. 8. Each distribution was best fitted with an exponential function defined by $$P(x) = \frac{1}{b} e^{(-\frac{x}{b})},$$

where b=mean(x) and x is the number of red blood cells per aggregate. Parameter b is thus an estimation of the mean number of red blood cells per 2D aggregate. $D_{OPT}$ was computed using Equation 17. Optical and acoustical estimations of D are compared in Table III. Microscopic images were acquired with a time resolution of 15 s. A time resolution of 30 s was used here to reduce the size of the table. Ultrasound data taken from FIG. 5 (RS0, H=6%) at corresponding times were used for comparison.

TABLE III

Comparison of estimations of D with the optical and ultrasonic methods.

| | Time (s) | | | | | | |
|---|---|---|---|---|---|---|---|
| | 0 | 30 | 60 | 90 | 120 | 150 | 180 |
| $D_{OPT}$ | 1.5 ± 0.3 | 2.4 ± 0.3 | 3.1 ± 0.5 | 3.5 ± 0.4 | 4.2 ± 0.2 | 4.5 ± 0.1 | 4.7 ± 0.1 |
| $D_{US}$  | 0.8 ± 0.1 | 3.9 ± 0.1 | 3.8 ± 0.6 | 5.3 ± 0.4 | 4.9 ± 1.0 | 4.8 ± 1.0 | 6.2 ± 1.1 |

Both methods show an increase of the aggregate size with time under static condition. The linear regression of $D_{OPT}$ with $D_{(US)}$ (see FIG. 9) resulted in an index of correlation $r^2=0.76$, reflecting that both methods allowed to follow the dimension of aggregates over time. As seen in FIG. 9, the optical method generally predicted lower values of D. Each point in FIG. 9 is the mean over three experiments at a particular time during the kinetics of aggregation.

On the Quality of the Data Normalization:

Firstly, three different transducers were used to obtain frequency dependent backscatter measurements. The continuity in frequency can be appreciated in FIGS. 3 and 6. Secondly, values of W obtained with the SFSE model of one embodiment the present invention for suspended non-aggregating red blood cells at 6% and 40% hematocrits are very close to the theoretical Perkus Yevick predictions. The estimated value of $D=0.78\pm0.09$ for H6 is also close to the expected number of 1 red blood cell/aggregate, whereas the size estimation seems slightly underestimated for H40 ($D=0.5\pm0.1$). Lastly, as another validation step, the increases in BSC reported here as a function of the level of aggregation and the low hematocrit data are comparable with published data from the literature. These results tend to demonstrate the validity of Equation 15 (normalization with $BSC_{H6}$) and of Equation 16 that were used to obtain $BSC_{T6}$, $BSC_{H40}$ and $BSC_{T40}$.

BSC Rate of Increase During Red Blood Cell Aggregation Kinetics:

As seen in FIG. 4, the BSC increase in the first few seconds following flow reduction was faster as the frequency was increased; this is especially evident for a hematocrit of 40% and for residual shear rates promoting the largest aggregates. These results confirm previous observations by the Applicant at 40% hematocrit. When comparing, in FIG. 4, results at 6% and 40% hematocrits, the more rapid increase of BSC at the highest hematocrit may be explained by the probability of two red blood cells to be in proximity being higher at 40% hematocrit.

Frequency Dependent Data and $2^{nd}$ Order Taylor Approximation (SFSE Model):

The first and second embodiments of the method 12 were limited to a $2^{nd}$ order Taylor expansion in Equation 8 as the Applicant found the surprising effect that the physical pertinence of the model was lost when a higher order was used. This is indeed surprising when one considers the theory that a higher polynomial order would provide a better fitting with the experimental data. For instance, the $2^{nd}$ order model allowed the estimation of W and D, which have a physical meaning. However, a skilled person would appreciate that higher orders may be used to obtain meaningful scatterer physical parameters, albeit less accurate. Also, higher orders may be more appropriate for different applications.

The Physical Meaning of W>1:

Equations 3 and 4 are functions of H and are strictly limited to $0<W\leq1$. Equations 3 and 4 were derived for non-aggregating particles. Moreover, the present results for non-aggregated red blood cells were consistent with these equations. As mentioned above, the packing factor W can be generalized for aggregating particles as the low frequency limit of the structure factor. The Baxter sticky hard sphere model in the field of colloidal suspensions has been used to describe the effect of aggregation within the Perkus Yevick approximation of the structure factor and its low frequency limit W (Regnaut C. and Ravey J. C., "Application of the adhesive sphere model to the structure of colloidal suspensions," Journal of Chemical Physics 91(2), 1211-1221 (1989)). The adhesive sphere model predicts values of W that decrease from 1 to 0 with increasing hematocrits for low adhesion energy, but presents values of W>1 when the adhesion energy is increased. Values of W up to 50 were reported at a volumic fraction of particles of 12%. The structure factor at a frequency of 0 Hz (i.e., S(0)=W) is thermodynamically described in this model as $W=mKT\xi_T$ with K being the Boltzmann's constant, T the absolute temperature and $\xi_T$ the isothermal compressibility.

Validation:

Although, there is no known way to experimentally characterize the real size of three-dimensional red blood cell aggregates at a physiological hematocrit, the dimensions reported here were validated in part by the microscopic observations. Also, quantitative information could be deduced with this first embodiment of the method 12 (SFSE method). It was clearly shown that the estimated parameters W and D were modulated in a predictable manner by the applied residual shear rate: higher shear rates produced smaller values of those measures due to the reversible disruption of red blood cell clusters. Furthermore, smaller values of W and D at 40% versus 6% hematocrit were shown.

Figure 10:
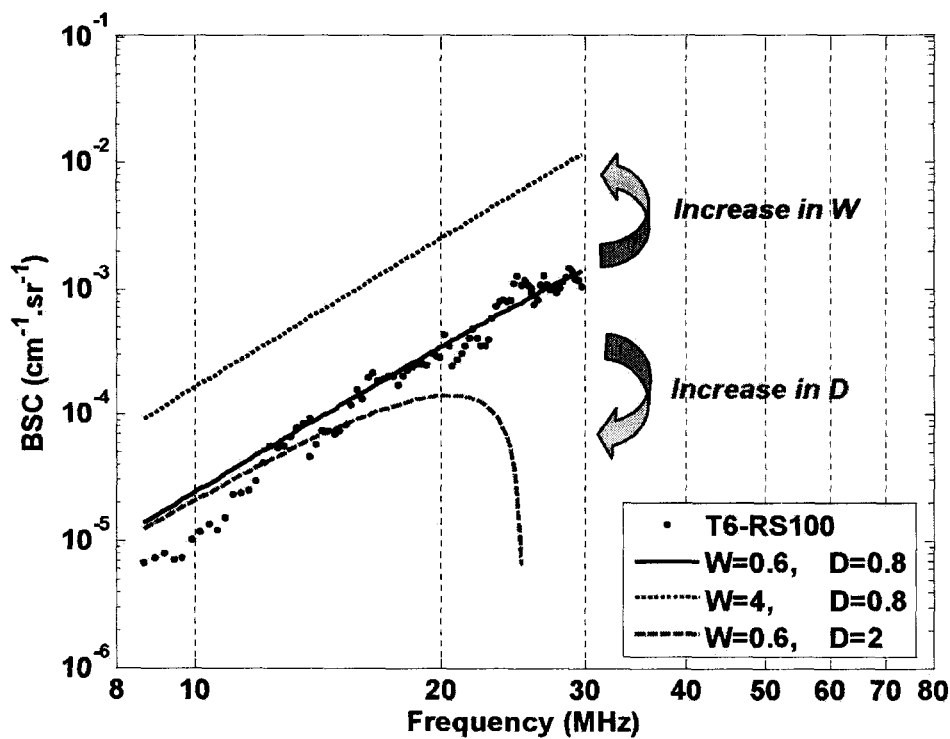
FIG. 10 is a graph from Example 1 illustrating the effect of increasing W and D on the BSC.

Respective Effect of W and D on the $2^{nd}$ Order Taylor Model—Relation $(D)^2 \rightarrow W$:

To assist the interpretation of the acoustical meaning of W and D and the relation between these two physical parameters, FIG. 10 is presented for T6-RS100 showing the respective effect of varying W and D on the BSC. The shear rate of $100 \, s^{-1}$ was selected arbitrarily although the same interpretation applies to the other shear rates. An increase in W has the effect of increasing the amplitude of the BSC at all frequencies. In terms of standard ultrasonic tissue characterization measures, it can be seen as an analogue to the mean BSC (Lizzi, F. L. et al "Theoretical framework for spectrum analysis in ultrasonic tissue characterization," Journal of the Acoustical Society of America 73(4), 1366-1373 (1983)). Increasing D has an effect on the frequency dependence and it thus modulates the spectral slope SS.

Figure 11:
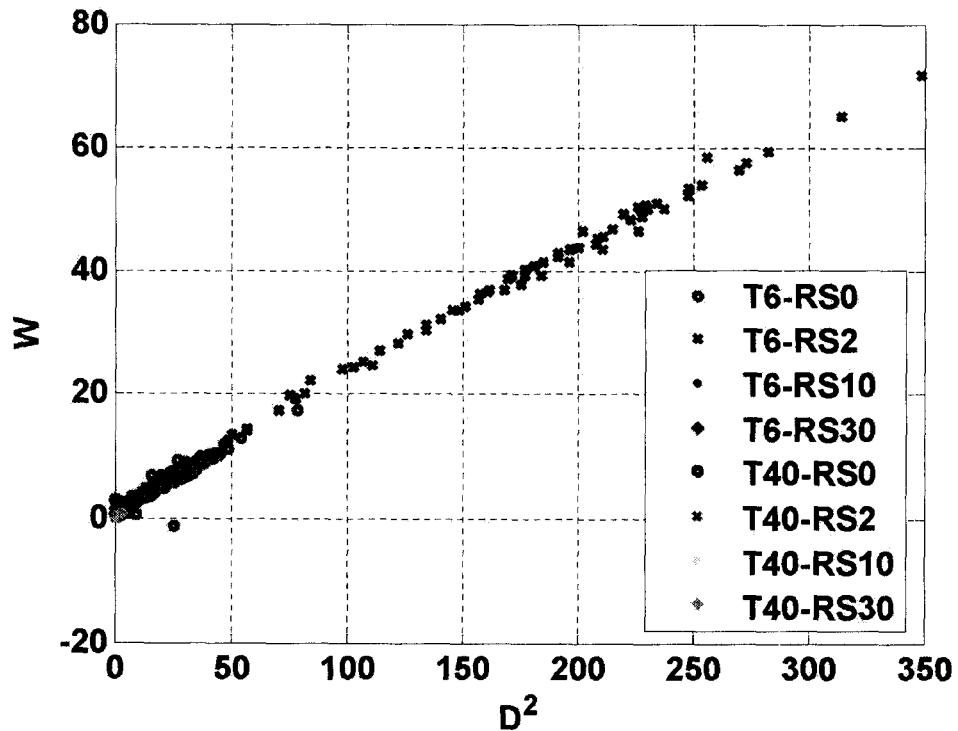
FIG. 11 is a graph from Example 1 illustrating a quadratic relationship between ultrasound determination of D and W for all shear rates (0, 2, 10 and 30 s$^{-1}$) at both 6% and 40% whole blood hematocrits.

Interestingly, parameters W and D, representing the "packing factor" and "normalized mean aggregate size" were not independent from one another. In FIG. 11 are plotted W as a function of $(D)^2$ for all blood samples tested during the entire kinetics of aggregation for 6% and 40% hematocrits and for all applied shear rates. It can be clearly seen that a quadratic relation exists between W and D. Those two parameters extracted from the frequency dependence of the backscattered ultrasound signal from aggregating red blood cells thus contain redundant information on the physical size of scatterers. Therefore, one of the parameters could be eliminated from the SFSE model of the present invention. However, it is advantageous to use both parameters as D brings a physical dimension and W is a parameter largely studied in ultrasonic blood characterization. The fact that the 40% hematocrit scales in the same way as the 6% hematocrit brings further confidence in the approximation model. FIG. 12 illustrates Guinier plots of T6 and T40 blood samples submitted to a residual shear of $2 \, s^{-1}$ with the cluster sizes D estimated using the Guinier plot reported in the legend.

This embodiment of the data reduction method of the present invention could provide many advantages over the classical first order spectral slope characterization of red blood cell aggregation. For instance, it more closely mimics the frequency dependence of BSC, it is physically interpretable in a non frequency dependent manner., and it could provide a basis for calibration of the acquisition and normalization procedures since redundant information is present in the model.

Example 2

This Example Illustrates In Vivo Results Obtained by the First Embodiment of the Method 12 to Obtain Information about Red Blood Cell Aggregation in a Brachial Vein of a Normal Subject A high frequency transducer (Visualsonics, Canada) was used to image the brachial vein of the normal subject's forearm. In this case, the RMV-710 probe was used (25 MHz center frequency, focal length 1.5 cm). The probe was positioned parallel to the vein of interest to provide a longitudinal section view of the vein. Each image contained 384 vertical lines. The equivalent to 10 images of the same section were digitized at a sampling frequency of 500 MHz. A region of interest was delimited around the venous valve. The data was processed as described for the first embodiment of the method 12, except that the power spectra were calculated on windows of 32 points positioned at 10 points intervals, for an overlap of 22 points. This allowed a 2D mapping of W and D over the image. Each estimate of W and D is based on the frequency fitting algorithm on the BSC (Equation 10 or 11) averaged over 10 images. The procedure could be performed on a single image but would be subject to higher noise. The size and overlapping of windows were not fixed to the reported values and can be changed depending on the desired resolution. Also, the BSC signal used in Equation 11 was firstly compensated for attenuation due to skin and underlying structure (e.g. muscle, fat, connective tissue). This attenuation compensation was computed using known equation 18:

$$BSC_{AttenuationCompesated} = BSC_{NonCompensated} \times e^{4 d_{tissue} \alpha_{tissue}} \quad (18)$$

where $d_{tissue}$=1.5 mm and $\alpha_{tissue}$=1 dB/cm/MHz.

Figure 13:
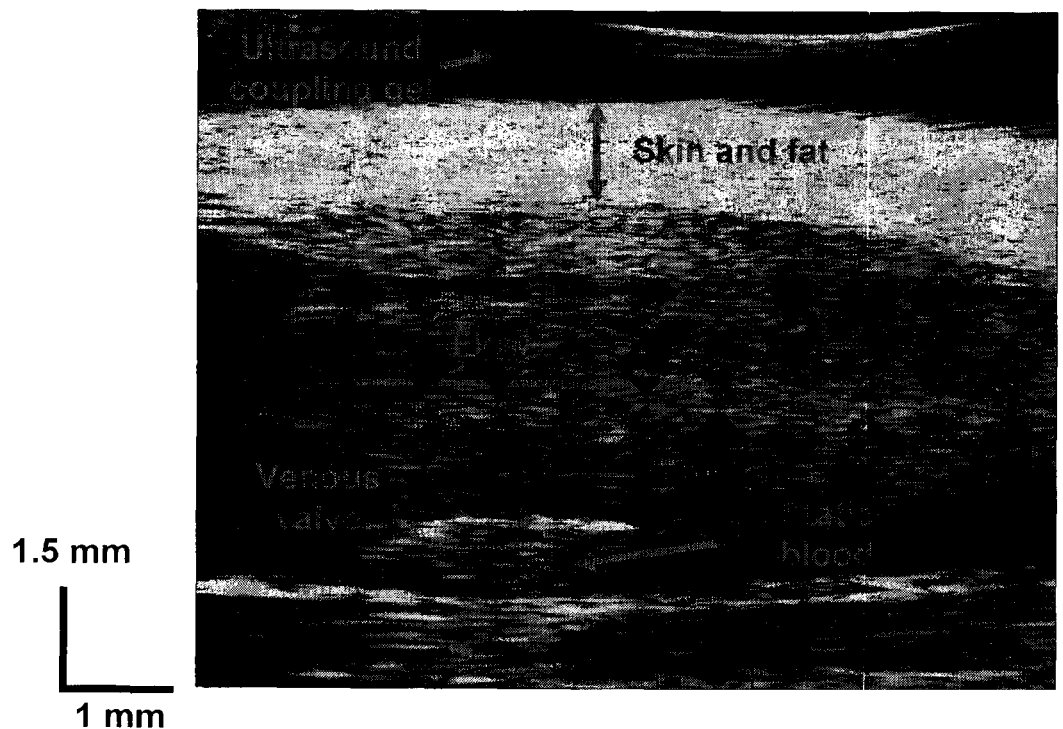
FIG. 13 is an ultrasound image of a vein of a forearm of a normal subject of Example 2.

A B-mode image of the vein is shown in FIG. 12. Parametrical images of the backscattering coefficient (BSC), spectral slope (SS), W and D over the same section are illustrated for comparison in FIG. 13. Mean values of these parameters shown in FIG. 15 for identified regions 1, 2 and 3 of FIG. 14. It can be appreciated that regions of stasis just behind the venous valves present higher values of W and D, as expected since stasis promotes aggregation. Lower values of W and D can be seen near the central region, were the flow is higher. These values of W≈0.1 and D≈0.5 quantitatively agree with low aggregation values.

Example 3

This Example Illustrates In Vitro Results Obtained from the Second Embodiment of the Method 12 where Attenuation and the Physical Parameters are Estimated Simultaneously with the SFSAE Model Blood Preparation:

Fresh porcine whole blood was obtained from a local slaughter house, centrifuged and the plasma and buffy coat were removed. Two blood samples were then prepared: (i) a H6 reference sample, which was a 6% hematocrit non-aggregating red blood cells resuspended in physiological saline solution; and (ii) a 40% hematocrit T40 test sample, which consisted of red blood cells resuspended in plasma to promote aggregation.

In Vitro Experiment in a Couette Flow System (Couette Device):

Ultrasound measurements were first performed in a Couette device to produce a linear blood velocity gradient at a given shear rate (FIG. 17). The system consists of a rotating inner cylinder with a diameter of 160 mm surrounded by a fixed concentric cylinder of diameter 164 mm. A 60 mL blood sample was sheared in the 2 mm annular space between the two coaxial cylinders. An ultrasound scanner (Vevo 770, Visualsonics, Canada) equipped with a RMV 710 probe was used in B-mode. The single-element focused circular transducer had a centre frequency of 25 MHz, a diameter of 7.1 mm and a focal depth of 15 mm. A sampling frequency of 250 MHz with 8 bits resolution was used (Gagescope, model 8500CS, Montreal, Canada). The probe was mounted in the side wall of the fixed outer cylinder and was positioned to have its focal zone at the centre of both cylinders. To ensure ultrasonic coupling, the hole within the outer stationary cylinder (containing the probe) was filled with a liquid agar gel based mixture. When solidified, this gel was cut to match the curvature of the cylinder to avoid any flow disturbance. The gel was a mixture of distilled water, 3% (w/w) agar powder (A9799, Sigma Chemical, USA), 8% (w/w) glycerol and a specific concentration of 50 µm cellulose scattering particles (S5504 Sigmacell, Sigma Chemical, USA) that determined the attenuation coefficient. Five experiments were performed with five mixtures having Sigmacell (SC) concentrations varying from 0% to 1% (w/w). The 0% concentration constituted the non-attenuating gel and the four other mixtures mimicked skin attenuations.

Prior to each measurement, the T40 blood was sheared at 200 $s^{-1}$ during 30 s to disrupt red blood cell aggregates. The shear rate was then reduced to residual values of 5, 10, 20, 30 and 50 $s^{-1}$ during 90 s to reach an equilibrium in the state of aggregation in the sheared blood sample. After that, for each shear rate, 20 B-mode images were constructed from acquired radio-frequency echoes for 80 s. For each line of the B-mode images, echoes were selected with a rectangular window of length 0.4 mm at twenty depths every 0.04 mm (i.e. with 90% overlap between windows). For each depth, the power spectra of the backscattered radio-frequency echoes were averaged over 20 acquisitions (corresponding to the 20 acquired images) to provide $P_{meas}$. This protocol was repeated five times with the five agar-based phantoms. Then, the T40 blood was removed and the H6 sample was introduced in the Couette device. The H6 sample was sheared at 50 $s^{-1}$ and coupled with the 0% SC concentration agar gel. Echoes were windowed as for the H40 sample at the same depths and their power spectra were averaged over 20 acquisitions to obtain $P_{ref}$. This reference power spectrum allows the normalization of the average power spectrum $P_{meas}$.

Figure 19:
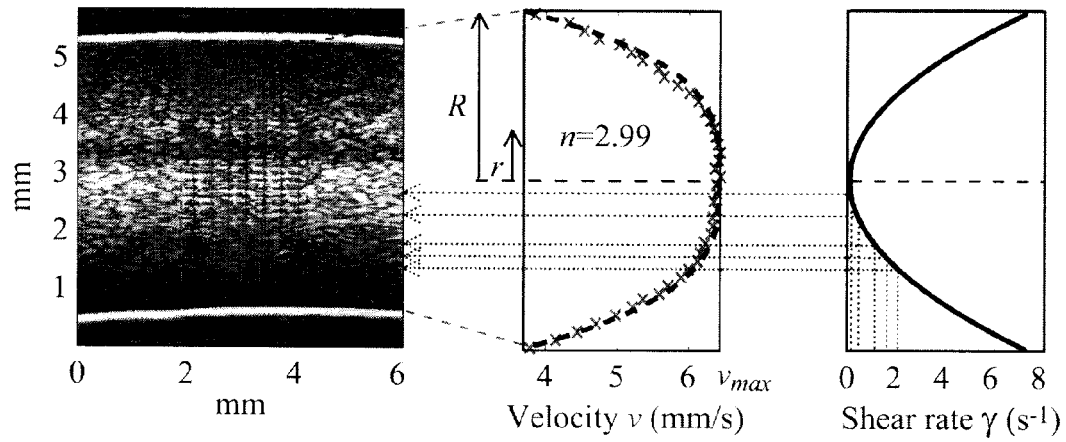
FIG. 19 illustrates estimates of particle displacement fields by speckle tracking (on the left) and corresponding mean velocity and shear rate as a function of depths in the tube (on the right), of Example 3.

In Vitro Experiments in a Tube:

In order to be closer to an in vivo condition, ultrasound measurements were also performed in a tubular flow device (FIG. 18). A constant pressure head was used to establish steady flow in a horizontal tube made of PVA (Polyvinyl Alcohol) cryogel thanks to a syringe pump (Harvard PHD 2000). The tube had an internal diameter of 4.5 mm and a length of 10 cm and was immersed in a tank filled with degassed water at room temperature. A layer of gel was placed between the probe and the tubular flow. Five experiments were performed with five mixtures having SC concentrations of: 0, 1, 1.5, 2 and 2.5% (w/w). The 0% concentration constituted the non-attenuating gel and the four other mixtures mimicked skin attenuations. FIG. 19 shows the displacement fields of red blood cells obtained from a speckle tracking method. The displacement of the speckle pattern between the frames was then related to velocity through the time between the images. As expected, the distribution of velocities was quasi-parabolic and the distribution of shear rates was deducted from this velocity profile by computing the derivative of velocities with respect to the tube radius.

Before entering the tube, the T40 sample blood was stirred in order to disaggregate red blood cells. The flow rate was chosen equal to 5 ml/min to promote the aggregation of red blood cells and when 30 ml of blood had circulated in the tube, 20 B-mode images were constructed for 80 s. For each line of the B-mode images, radio-frequency echoes were selected with a rectangular window of length 0.4 mm at 65 depths every 0.04 mm (i.e. with 90% overlap between windows). For each depth, the power spectra of the backscattered echoes were averaged over 20 acquisitions (corresponding to the 20 acquired images) to provide $P_{meas}$. This protocol was repeated five times with the five agar-based phantoms. A reference measurement was performed by using the stirred H6 sample. Echoes were windowed as for the H40 sample at the same depths and their power spectra were averaged over 20 acquisitions to obtain $P_{ref}$. This reference power spectrum allowed the normalization of the average power spectrum $P_{meas}$.

Attenuation Measurements:

The attenuation coefficients of the reference (0% SC) and of the other skin-mimicking phantoms $\alpha_{sc}$ were determined by using a standard substitution method. A scanner equipped with a transducer with centre frequency of 25 MHz (Vevo 770, Visualsonics, Canada) was used in transmission/reception with a reflector on the opposite side of the phantom for reflection measurements. Reflected signals were recorded both with and without the agar gel sample in the acoustic path. The attenuation coefficient was then estimated using a log spectral difference technique as described in R. Kuc and M. Schwartz, "Estimating the acoustic attenuation coefficient slope for liver from reflected ultrasound signals", IEEE Transactions on Sonics & Ultrasonics SU-26, pp. 353-362, 1979. For each concentration of SC, six regions were scanned for averaging purpose. Thicknesses of skin-mimicking phantoms $e_{sc}$ were fixed to 10 mm in the case of the Couette device and 5 mm in the case of the tube flow device. As shown in Table IV, attenuation coefficients of skin-mimicking phantoms were in the same range as the human dermis (which is 0.21 dB/MHz at 14-50 MHz considering a 1 mm dermis thickness).

TABLE IV

Attenuation coefficient measurements of skin-mimicking phantoms for the Couette and tubular flow devices.

| SC (%) | $\alpha_{sc}$ for Couette device (dB/MHz) | $\alpha_{sc}$ for tube flow device (dB/MHz) |
|---|---|---|
| 0 | 0.070 ± 0.020 | 0.035 ± 0.01 |
| 0.25 | 0.115 ± 0.024 | — |
| 0.5 | 0.219 ± 0.030 | — |
| 0.75 | 0.320 ± 0.035 | — |
| 1 | 0.411 ± 0.040 | 0.206 ± 0.021 |
| 1.5 | — | 0.310 ± 0.035 |
| 2 | — | 0.412 ± 0.034 |
| 2.5 | — | 0.501 ± 0.039 |

The attenuations $\alpha_{blood}$ of the blood sheared at different shear rates were also measured in reflection mode using the same Couette device configuration. The gel had a 0% SC concentration and the rotating inner cylinder was used as the reflector (Table V).

TABLE V

Measurements of the attenuation coefficient of blood for different shear rates.

| Shear rate ($s^{-1}$) | $\alpha_{blood}$ (dB/MHz) |
|---|---|
| 5 | 0.053 ± 0.011 |
| 10 | 0.036 ± 0.008 |
| 20 | 0.024 ± 0.005 |
| 30 | 0.016 ± 0.003 |
| 50 | 0.015 ± 0.003 |

Reference Measurements with the 0% SC Concentration Phantom

The experiment with the 0% SC phantom was realized in order to have reference results of packing factors $W_{ref}$ and aggregate diameters $D_{ref}$ obtained with the SFSE model when considering predetermined values of blood attenuation. These parameters were assumed to be true values of packing factors and aggregate diameters at all shear rates, and were compared with packing factors and diameters estimated by the SFSAE and SFSE models when skin-mimicking phantoms were used. The H6 reference sample was also measured with the 0% SC phantom. The phantom attenuation, although small when no SC was used, therefore affected equivalently both spectra $P_{meas}$ and $P_{ref}$ in Equation 14. The resulting measured backscatter coefficient $BSC_{ref}$ was thus not biased by gel attenuation.

Results Obtained with In Vitro Experiments in the Couette Device

FIG. 22 illustrates the minimization of the cost function in the SFSAE model.

Reference Parameters with the SFSE Model:

FIG. 21 illustrates $W_{ref}$ and $D_{ref}$ obtained from the SFSE model with compensation for blood attenuation in the case of no gel attenuation. The amplitude of the backscatter coefficient as well as the estimation of the parameters $W_{ref}$ and $D_{ref}$ decreases as the shear rate increases (i.e. when the level of aggregation becomes smaller).

Figure 23:
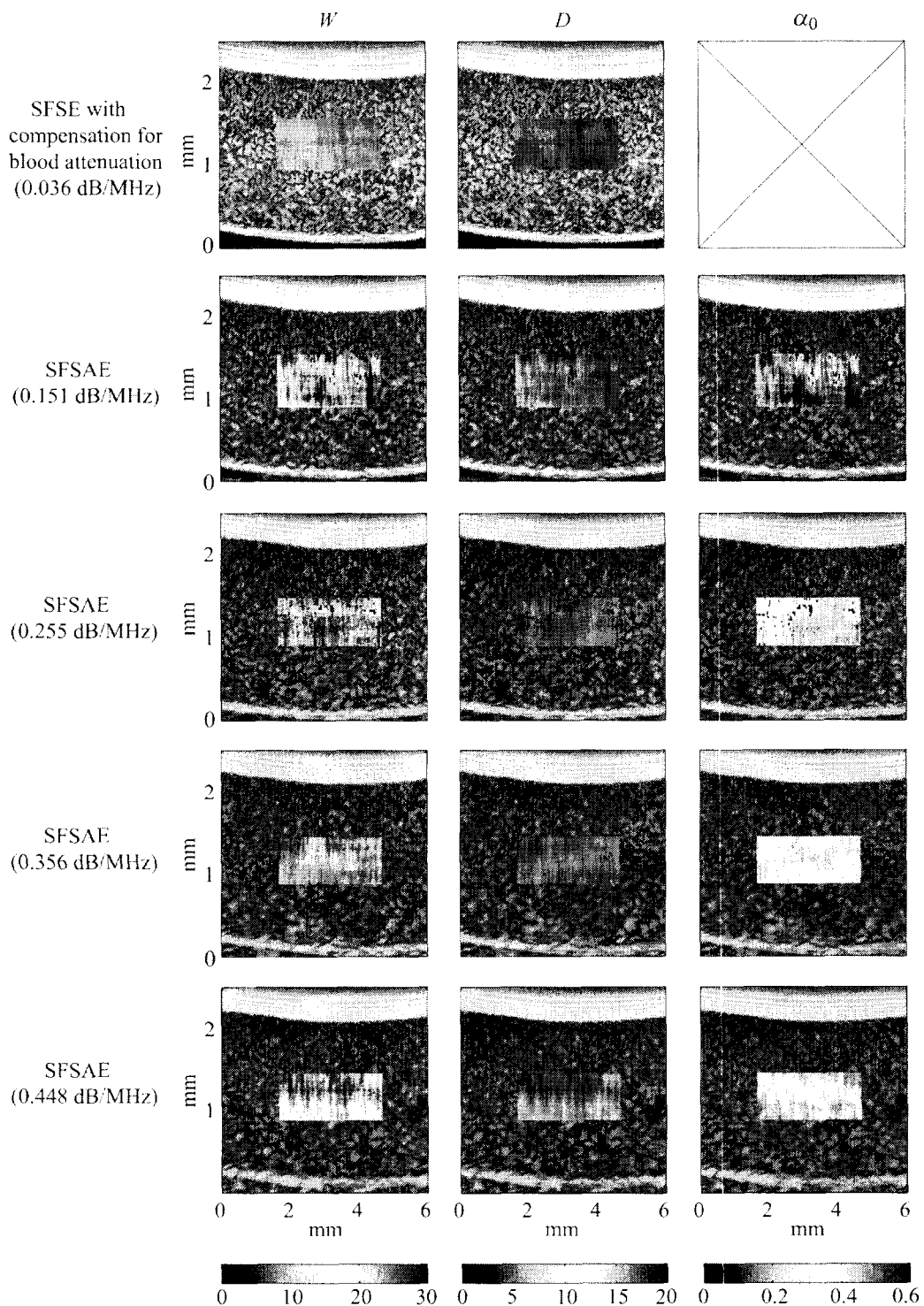
FIG. 23 shows quantitative images from Example 3 of blood sheared at 10 s$^{-1}$ in a Couette device superimposed on gray-scale B-mode images with W and D estimated by the SFSE model with compensation for blood attenuation for the non-attenuating phantom (top row) and by the SFSAE model for the four attenuating phantoms with $\alpha_0$ varying between 0.151-0.448 dB/MHz.
Figure 24:
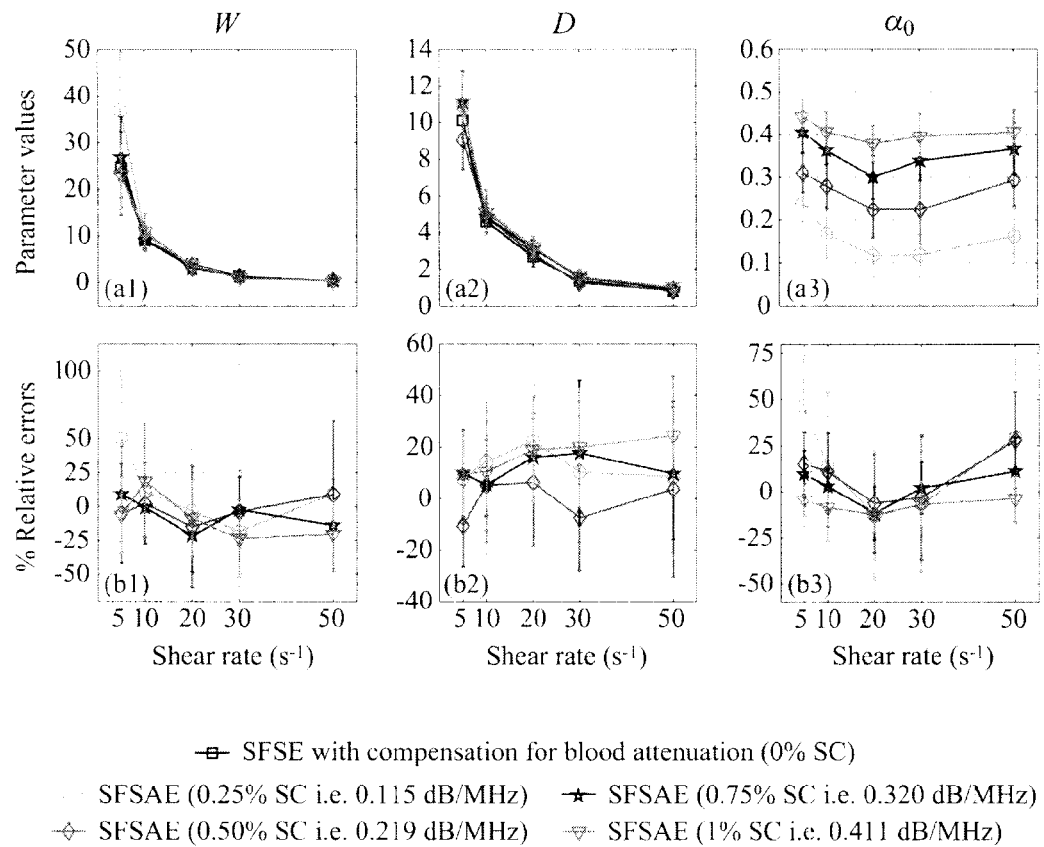
FIG. 24 illustrates graphs from Example 3 of values of W, D and $\alpha_0$ (in dB/MHz) and corresponding relative errors for different residual shear rates estimated by the SFSE model with compensation for blood attenuation for no attenuation phantom and by the SFSAE model for the four attenuating phantoms, where SC indicates the concentration of Sigmacell particles in the phantom.

Parameters Evaluated with the SFSAE:

Typical results obtained when applying the SFSAE model for the different agar phantoms at a shear rate of 10 $s^{-1}$ and 50 $s^{-1}$ are illustrated in FIG. 22. For both shear rates, it can be observed that as the total attenuation increases, the more the backscatter coefficient amplitude decreases at all frequencies and the more the frequency dependence of the backscattering coefficient changes. The parameters W and D from the SFSAE model are very similar to the reference parameters $W_{ref}$ and $D_{ref}$. The total attenuations $\alpha_0$ estimated with the SFSAE are also similar to the reference total attenuation measured independently. The reference total attenuations $\alpha_{ref}$ correspond to those obtained with $\Sigma \alpha_i e_i = \alpha_{sc} e_{sc} + \alpha_{blood} e_{blood}$ where $\alpha_{sc}$ and $\alpha_{blood}$ are the skin-mimicking phantom attenuation and the blood attenuation estimated in the reflection mode. FIG. 23 shows quantitative images superimposed on the gray-scale B-mode images of the blood sheared at 10 $s^{-1}$ in the Couette device. The colour of each pixel was assigned based on the value of the parameters estimated by the SFSE with the 0% SC phantom and by the SFSAE with the four skin-mimicking phantoms, associated with that pixel. The colour bars relate the pixels in the quantitative images to the estimated parameters (W, D and $\alpha_0$) in a chosen region-of-interest. The black pixels in the quantitative images correspond to rejected solutions of the optimization method (when the estimated diameter D was found <<0.1, which is unrealistic). A clear distinction between images of the estimated total attenuation with the four skin-mimicking phantoms is apparent, whereas images of the estimated parameters W and D are quite similar. For each residual shear rate, quantitative images for the three parameters W, D and $\alpha_0$ were constructed and mean values were calculated. FIG. 24 summarizes these results. In this figure, the relative errors for each parameter correspond to: $(W-W_{ref})/W_{ref}$, $(D-D_{ref})/D_{ref}$ and $(\alpha_0-\alpha_{ref})/\alpha_{ref}$. Except for the shear rate 5 s$^{-1}$ with the skin-mimicking phantom having the smallest attenuation (0.25% SC), the SFSAE gave quantitatively satisfactory estimates of W and D with relative errors below 25%.

Figure 25:
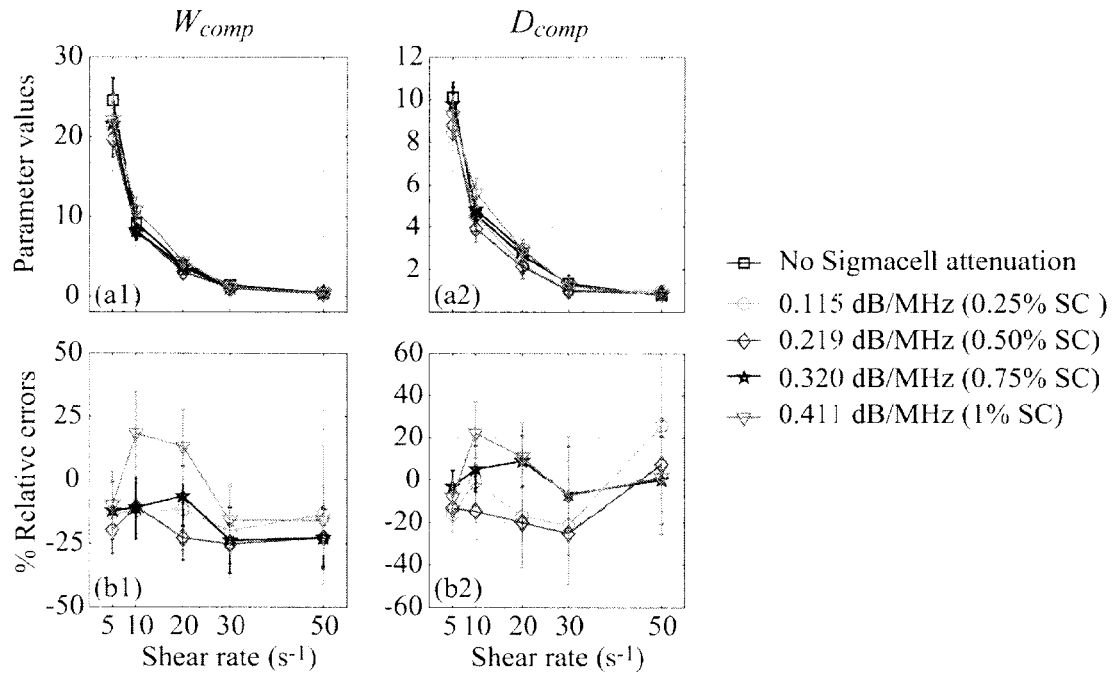
FIG. 25 illustrates graphs from Example 3 of values of $W_{comp}$ and $D_{comp}$ and corresponding relative errors for different residual shear rates estimated by the SFSE model with compensation for blood attenuation for the live phantoms.

Parameters Evaluated with the SFSE with a Priori Compensation for Blood Attenuation The packing factor $W_{comp}$ and the diameter of the aggregates $D_{comp}$ were also evaluated by compensating the backscatter coefficients in the SFSE with the predetermined values measured independently in reflection mode. Results are presented in FIG. 25. The relative errors are below 25% for all shear rates and all skin-mimicking phantoms.

Results Obtained with In Vitro Experiments in the Tubular Flow Device

Figure 26:
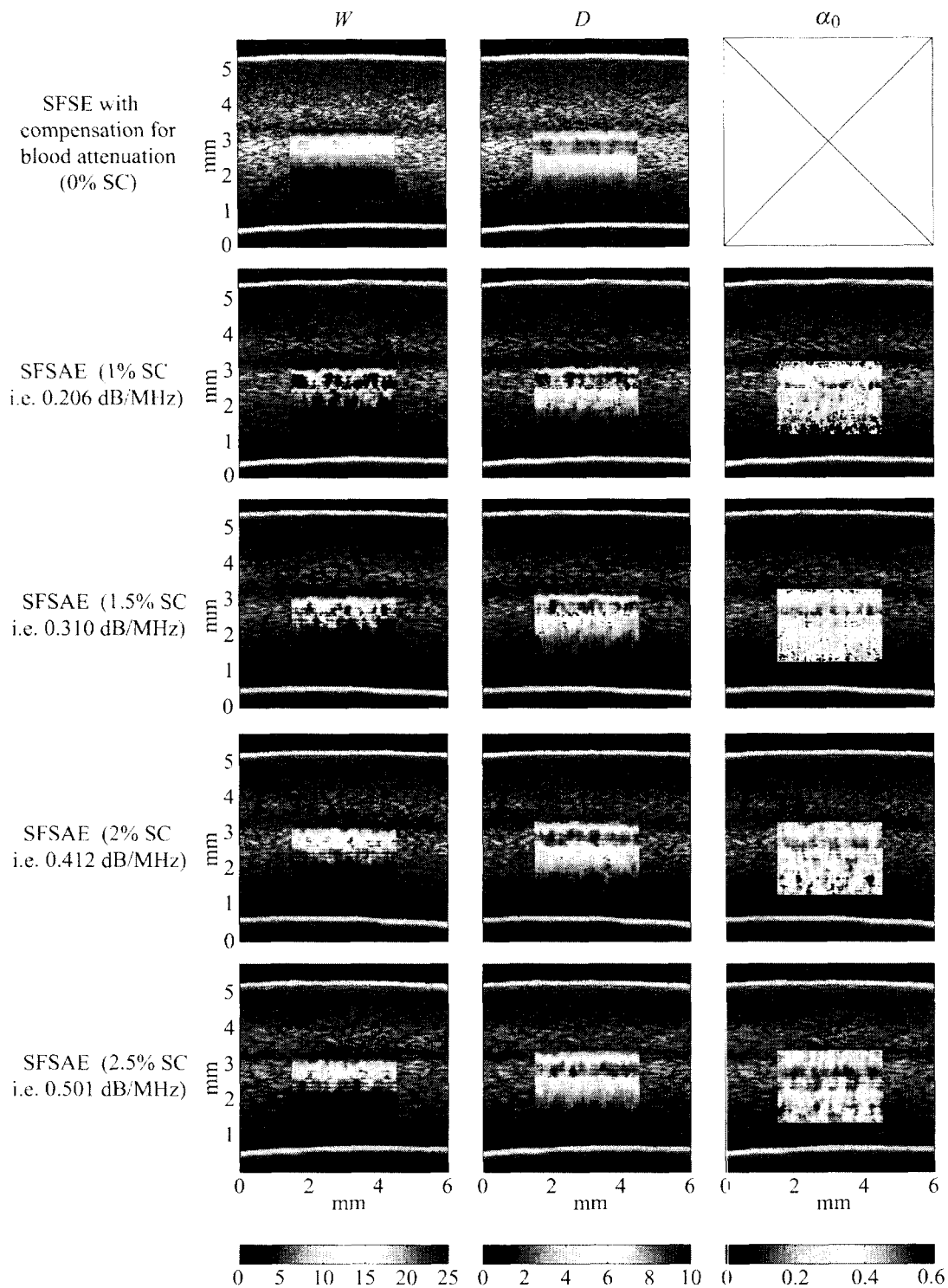
FIG. 26 shows quantitative images from Example 3 of blood sheared in a cylindrical tube superimposed on gray-scale B-mode images with W and D estimated by the SFSE model with compensation for blood attenuation for the non-attenuating phantom (top row) and by the SFSAE model for the four attenuating phantoms.
Figure 27:
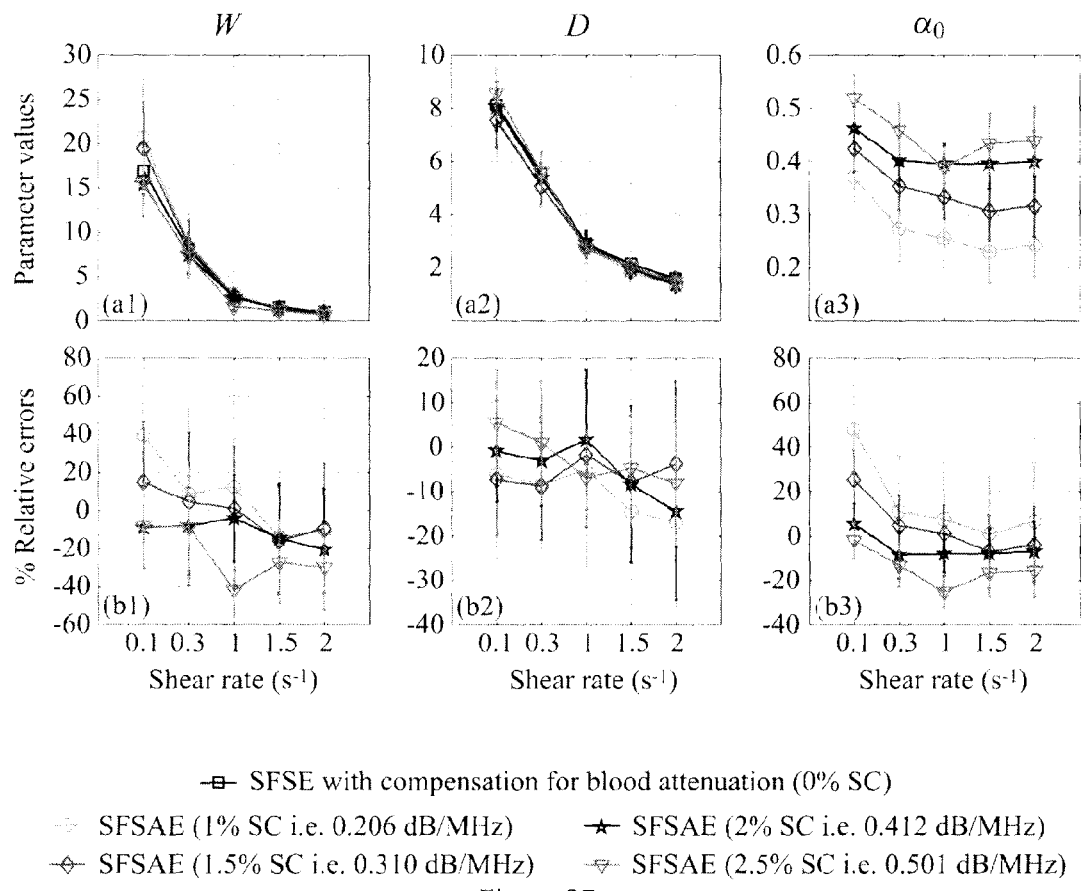
FIG. 27 illustrates graphs from Example 3 or values of W, D and $\alpha_0$ (in dB/MHz) and corresponding relative errors for different shear rates in the tube experiment where the parameters were estimated by the SFSE model with compensation for the non-attenuating phantom and by the SFSAE model for the four attenuating phantoms.

FIG. 26 shows quantitative images superimposed on the gray-scale B-mode images of blood in the tubular flow device for each skin-mimicking phantom. As observed in the Couette device experiments, a clear distinction between images of the estimated total attenuation with the four skin-mimicking phantoms is apparent, whereas images of the estimated parameters W and D are quite similar, as desired. Nevertheless, images of the estimated total attenuation are less homogeneous compared to those obtained in the Couette device. For several depths in the image corresponding to specific shear rates, mean values of the three parameters W, D and $\alpha_0$ were calculated. FIG. 27 summarizes these results. The SFSAE gave estimates of W and D with relative errors below 20% for all shear rates and for total attenuations of 0.310 dB/MHz (1.5% SC) and 0.412 dB/MHz (2% SC). Worse estimates were obtained at 0.1 s$^{-1}$ for the smallest attenuation (1% SC i.e. 0.206 dB/MHz) and at 1 s$^{-1}$ for the highest attenuation (2.5% SC, i.e. 0.501 dB/MHz): relative errors for the estimation of W were around 40%. For shear rates between 0.3 and 3 s$^{-1}$, the worse results of W, D and $\alpha_0$ were obtained for the highest attenuation (2.5% SC i.e. 0.501 dB/MHz).

Comparison of the SFSAE and of the SFSE with a Priori Compensation for Attenuation For the Couette device experiment, the accuracy of the estimates obtained with the SFSAE was as satisfactory as those obtained with the SFSE with attenuation-compensation (i.e. when a priori are known about the attenuation). For both methods, relative errors for W and D were below 25%, except for one value corresponding to the shear rate of 5 s$^{-1}$ with the skin-mimicking phantom having the smallest attenuation (0.25% SC). In this last case, the SFSAE gave less accurate estimates (relative errors around 50% for W and $\alpha_0$). Nevertheless, the SFSAE has the major advantage to be easily applicable in vivo because of the simultaneous estimation of the blood structural properties and total attenuation (contrary to the SFSE attenuation-compensation method, needing the attenuation and thickness of the tissue intervening layers to be known).

Limitations of the SFSAE as a Function of Ka and of the Total Attenuation

For both Couette and tubular flow devices, the SFSAE gave less accurate estimates for the smallest shear rates (i.e. the highest aggregated cases) and the smallest attenuations (0.115 dB/MHz for the Couette device and 0.206 dB/MHz for the tube). In FIGS. 24 and 27, relative errors for $\alpha_0$ are always worse at these smallest shear rates for all skin-mimicking phantoms, especially in the tube experiments. At 5 s$^{-1}$ for the Couette experiments and at 0.1 s$^{-1}$ for the tube experiments, the SFSE and consequently the SFSAE seemed to reach their limit of applicability for large aggregate sizes: for the Couette device experiment, this typically corresponds to $D_{ref}$=10.11 in FIG. 21 (i.e. ka=2.8) and for the tube experiment, it is typically obtained for $D_{ref}$=8.13 (i.e. ka=2.23). This limit is illustrated by the bad fit of the SFSE model in FIG. 21 at 5 s$^{-1}$. In the tube flow experiments, for shear rates between 0.3 and 3 s$^{-1}$, the worse results of W, D and $\alpha_0$ were obtained for the highest attenuation (2.5% SC i.e. 0.501 dB/MHz) (see FIG. 27). To conclude, the SFSAE performed well for ka<2.23 (i.e. D=8) and for total attenuations ranging between 0.115 and 0.412 dB/MHz. Although the SFSAE gave less accurate estimates for the attenuation of 0.501 dB/MHz and for ka≤2.23, the estimated parameter values presented in FIGS. 24 and 27 show that the SFSAE gave qualitatively satisfactory estimates for all skin-mimicking phantoms at all shear rates, since the estimates of W and D versus shear rates had the same behaviour as $W_{ref}$ and $D_{ref}$.

The SFSAE model has the advantage that it is easily applicable in vivo because of the simultaneous estimation of the scatterer structural properties and the total attenuation (contrary to existing attenuation-compensation methods which require the attenuation and thickness measurements of the tissue intervening layers). This work thus confirms the in vivo applicability of red blood cell aggregate size and attenuation estimations.

Example 4

Figure 28:
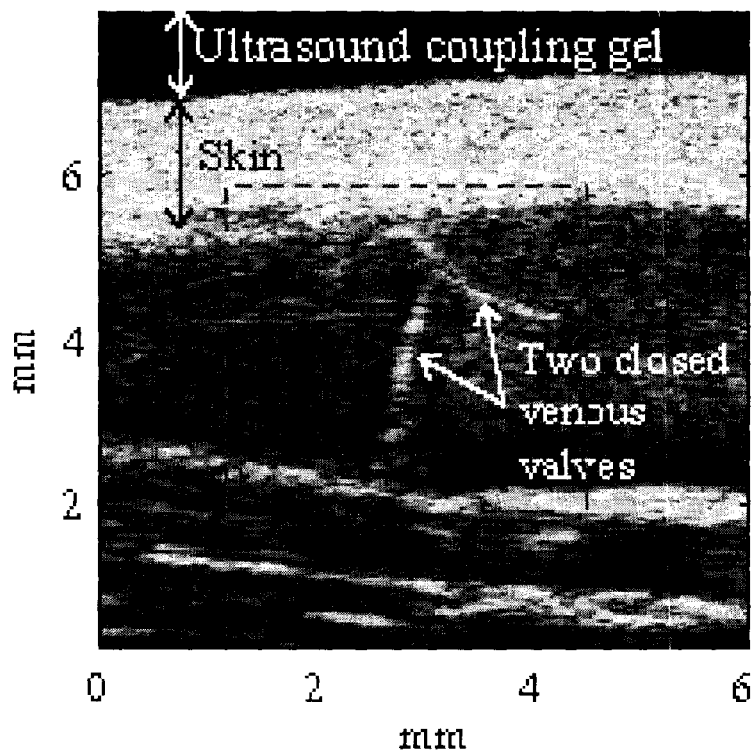
FIG. 28 is an ultrasound image of a vein of a healthy subject of Example 4.
Figure 29:
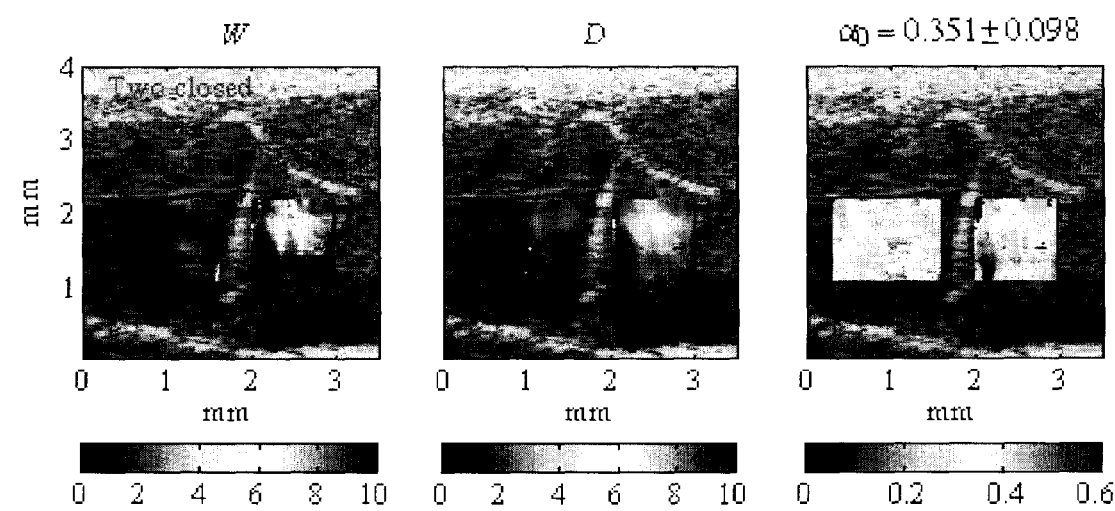
FIG. 29 shows the image of FIG. 28 with quantitative images estimated by the SFSAE model.

This Example Illustrates Results from an In Vivo Application of the Second Embodiment of the Method 12 to a Healthy Patient FIG. 28 illustrates a B-mode ultrasound image of two closed venous valves in a vein in an arm of a normal subject acquired according to the second embodiment of the method of the present invention. FIG. 29 illustrates quantitative images of three parameters (W, D and $\alpha_0$) estimated by this embodiment superimposed on the B-mode image of FIG. 28. As expected, the values of W and D are more important at a region where the blood stagnates (area behind the venous valve) as it is known that stagnation promotes red blood cell aggregation.

It should be appreciated that the invention is not limited to the particular embodiments described and illustrated herein but includes all modifications and variations falling within the scope of the invention as defined in the appended claims. For example, it will be clear to a skilled person, from the description herein and Examples 1-4 that embodiments of the present invention can be applied to obtain quantitative and qualitative physical parameter values of scatterers in a medium, with and without simultaneous estimation of attenuation, and to monitor these physical parameters in real-time. It will also be clear that ultrasound imaging is not required for obtaining values of W and D (and equivalently $\alpha_0$, i or any other physical parameters describing blood). For instance, ultrasound signals can be recorded without imaging, the computation performed and the values of W and D displayed for evaluation. Furthermore, the present invention is not limited to blood or the monitoring of red blood cells and can be applied to characterize any scatterers in a medium. Also, the phraseology and terminology used herein is for the purpose of description and should not be regarded as limiting. The use of "including", "comprising", or "having", "containing", "involving" and variations thereof herein, is meant to encompass the items listed thereafter as well as additional items.

The invention claimed is:

1. A method for characterizing ultrasound scatterers in a medium, the scatterers including red blood cells and clusters of red blood cells in blood, the method comprising:
    detecting in vivo ultrasound data from a pulser-receiver and a wideband ultrasound transducer representing a region of interest comprising a plurality of scatterers in a medium, the plurality of scatterers including clusters of scatterer sub-units being clusters of red blood cells, the scatterers having a physical property value to be estimated and the scatterer sub-units having at least one known physical parameter value;
    modelling a backscatter coefficient of the ultrasound data using an at least second order function based on a Taylor expansion of a frequency dependence of a structure factor, the frequency dependence of the structure factor being related to a Fourier transform of a pair correlation function in a system of scatterers, the pair correlation function defining a probability of finding a scatterer at a determined distance from another scatterer;
    estimating the physical property value of the scatterers from ultrasound data as modelled and the at least one known physical parameter of the scatterer sub-units by a fitting regression of the backscatter coefficient as a function of frequency; and
    monitoring red blood cell aggregation in blood from the physical property value.

2. A method according to claim 1, wherein modelling the backscatter coefficient of the ultrasound data is based on a Born approximation.

3. A method according to claim 1, wherein the fitting regression is a least squared approximation.

4. A method according to claim 3, wherein the least squared approximation is a polynomial fitting.

5. A method according to claim 1, wherein the physical property to be estimated is at least one selected from the group consisting of a packing factor W of the scatterers in the medium, a diameter D of the scatterers, a volume concentration H of the scatterers in the medium, a fractal size d of the scatterers, and the pair correlation function g(r) of the scatterers.

6. A method according to claim 5, wherein the at least one known physical parameter is at least one selected from the group consisting of a radius a of the scatterer sub-units, an acoustic impedance mismatch C between the medium and the scatterer sub-units, and a density, a compressibility and a speed of sound c of the medium and the scatterer sub-units.

7. A method according to claim 6, wherein the at least one known physical parameter is the radius a of the scatterer sub-units and the acoustic impedance mismatch C between the medium and the scatterer sub-units, or the at least one known physical parameter is the radius a of the scatterer sub-units and at least two selected from the group consisting of the impedance C, the speed of sound, the density and the compressibility of the medium and the scatterer sub-units.

8. A method according to claim 7, wherein the physical property value to be estimated is the packing factor W and the diameter D of the scatterers, the method comprising applying:

$$BSC(-2k) = \frac{1}{3\pi}HC^2k^4a^3\left[3\frac{\sin(2ka)-2ka\cos(2ka)}{(2ka)^3}\right]^2 \times [W - 2.4D^2a^2k^2]$$

where BSC is the backscatter coefficient and k is a wave vector.

9. A method according to claim 1, further comprising obtaining ultrasound radio-frequency signals, digitizing said ultrasound radio-frequency signals, Fourier transforming the ultrasound radio-frequency signals as digitized and squaring the amplitude to obtain the ultrasound data.

10. A method according to claim 9, further comprising transmitting ultrasound energy into the region of interest to obtain the ultrasound radio-frequency signals.

11. A method according to claim 1, wherein the modelling includes consideration of an attenuation of the scatterers and the medium, the method further comprising estimating the attenuation at the same time as estimating the physical property value of the scatterers when modelling the backscatter coefficient of the ultrasound data in which:

$$BSC(-2k) = \frac{1}{3\pi}HC^2k^2a^3\left[3\frac{\sin(2ka)-2ka\cos(2ka)}{(2ka)^3}\right]^2 \times [W - 2.4D^2a^2k^2]A(-2k)$$

where A is the frequency dependant attenuation coefficient.

12. A method according to claim 11, wherein simultaneously estimating the attenuation and the physical property value comprises minimizing a cost function which is a mean quadratic difference between the ultrasound data provided and the ultrasound data as modelled.

13. A method according to claim 1, further comprising normalizing the ultrasound data before modelling.

14. A method according to claim 1, wherein monitoring red blood cell aggregation is performed to monitor inflammation of a patient.

15. A method for characterizing ultrasound scatterers in a medium, the scatterers including red blood cells and clusters of red blood cells in blood, the method comprising:
    detecting ultrasound data from a pulser-receiver and a wideband ultrasound transducer representing a region of interest comprising a plurality of scatterers in a medium, the plurality of scatterers including clusters of scatterer sub-units, the scatterers having a physical property value to be estimated and the scatterer sub-units having at least one known physical parameter value;
    modelling a backscatter coefficient of the ultrasound data using an at least second order function based on a Taylor expansion of a frequency dependence of a structure factor, the frequency dependence of the structure factor being related to a Fourier transform of a pair correlation function in a system of scatterers, the pair correlation function defining a probability of finding a scatterer at a determined distance from another scatterer;
    simultaneously estimating an attenuation of the scatterers and of the medium and the physical property value of the scatterers from the modelled ultrasound data and the at least one known physical parameter of the scatterer sub-units by a mean quadratic difference between the ultrasound data provided and ultrasound data as modelled; and
    monitoring red blood cell aggregation in blood from the physical property value.

16. A method according to claim 15, wherein monitoring red blood cell aggregation is performed to monitor inflammation of a patient.

17. A system for characterizing ultrasound scatterers in a medium, the scatterers including red blood cells and clusters of red blood cells in blood, the system comprising:
    a transmitter for transmitting an in vivo ultrasound signal to a region of interest, the region of interest comprising a plurality of scatterers in a medium, the plurality of scatterers including clusters of scatterer sub-units being clusters of red blood cells, the scatterers having a physical property value to be estimated and the scatterer sub-units having at least one known physical parameter value;

at least one detector for detecting a scattered or a backscattered ultrasound signal; and a processor for monitoring red blood cell aggregation in blood from the physical property value by converting the detected ultrasound signal to ultrasound data representing the region of interest, modelling a backscatter coefficient of the ultrasound data using an at least second order function based on a Taylor expansion of a frequency dependence of a structure factor, the frequency dependence of the structure factor being related to a Fourier transform of a pair correlation function in a system of scatterers, the pair correlation function defining a probability of finding a scatterer at a determined distance from another scatterer, and estimating the physical property value of the scatterers from ultrasound data as modelled and the at least one known physical parameter of the scatterer sub-units by a regression of the backscatter coefficient as a function of frequency.

18. A system according to claim 17, further comprising an alert means for indicating when the estimated physical property value of the scatterers matches, approaches, falls below or falls above a predefined value.

19. A system according to claim 17, wherein the processor monitors red blood cell aggregation to monitor inflammation of a patient.

* * * * *